(12) United States Patent
Jaworski et al.

(10) Patent No.: US 6,307,128 B1
(45) Date of Patent: Oct. 23, 2001

(54) FATTY ACID ELONGASES

(75) Inventors: Jan G. Jaworski, Oxford, OH (US); Martha Ann Post-Beittenmiller, Ardmore, OK (US); James Todd, Oxford, OH (US)

(73) Assignees: Miami University, Oxford, OH (US); Samuel Roberts Noble Foundation, Ardmore, OK (US)

( * ) Notice: Subject to any disclaimer, the term of this patent is extended or adjusted under 35 U.S.C. 154(b) by 0 days.

(21) Appl. No.: 08/868,373

(22) Filed: Jun. 3, 1997

(51) Int. Cl.$^7$ .............................. A01H 5/00; C12N 15/82
(52) U.S. Cl. .................... 800/298; 800/281; 435/419; 536/23.6
(58) Field of Search ................. 800/298, 281; 435/69.1, 419, 320.1; 536/23.6

(56) References Cited

U.S. PATENT DOCUMENTS

| | | | |
|---|---|---|---|
| 5,041,382 | 8/1991 | Gupta et al. | 435/240.45 |
| 5,122,466 | 6/1992 | Stomp et al. | 435/172.3 |
| 5,188,958 | 2/1993 | Moloney et al. | 435/240.4 |
| 5,204,253 | 4/1993 | Sanford et al. | 435/172.3 |
| 5,445,947 | 8/1995 | Metz et al. | 435/69.1 |
| 5,484,956 | 1/1996 | Lundquist et al. | 800/205 |
| 5,550,318 | 8/1996 | Adams et al. | 800/205 |
| 5,679,881 | 10/1997 | Metz et al. | 800/205 |
| 6,124,524 | * 9/2000 | James et al. | 800/281 |

FOREIGN PATENT DOCUMENTS

| | | |
|---|---|---|
| WO 93/10241 | 5/1993 | (WO) . |
| WO 94/11516 | 5/1994 | (WO) . |
| WO 95/15387 | 6/1995 | (WO) . |
| WO 96/13582 | 5/1996 | (WO) . |

OTHER PUBLICATIONS

James, Jr. et al., "Directed Tagging of the Arabidopsis Fatty Acid Elongation1 (FAE1) Gene with the Maize Transposon Activator", *The Plant Cell*, vol. 7, 309–319, 1995.

Millar, A., et al., "The Products of the Microsomal Fatty Acid Elongase Are . . . of the Condensing Enzyme," *Physiology, Biochemistry and Molecular Biology of Plant Lipids*, Kluwer Academic Press, pp. 72–74 (1997).

Xia, Y., et al., "Cloning and Characterization of CER2, an Arabidopsis Gene That Affects Cuticular Wax Accumulation," *The Plant Cell*, 8:1291–1304 (1996).

Hlousek–Radojcic, A., et al., "Oleoyl–CoA is not an immediate substrate for fatty acid elongation in developing seeds of *Brassica napus*," *The Plant Journal*, 8(6):803–809 (1995).

* cited by examiner

*Primary Examiner*—Elizabeth F. McElwain
(74) *Attorney, Agent, or Firm*—Fish & Richardson P.C., P.A.

(57) ABSTRACT

Nucleic acids are disclosed that encode fatty acid β-keto acyl synthases from plants. Such synthases are effective for producing very long chain fatty acids (VLCFA), e.g., C22 to C26, preferentially saturated but also monounsaturated. Also disclosed are polypeptides encoded by such nucleic acids. Transgenic plants expressing these polypeptides exhibit altered levels of VLCFA in one or more tissues, such as seeds or leaves.

64 Claims, 16 Drawing Sheets

FAE1 w/ respect to time

```
EL1    1560 bases
ATGGATCGAG AGAGATTAAC GGCGGAGATG GCGTTTCGAG ATTCATCATC GGCCGTTATA
AGAATTCGAA GACGTTTGCC GGATTATTA ACGTCCGTTA AGCTCAAATA CGTGAAGCTT
GGACTTCACA ACTCTTGCAA CGTGACCACC ATTCTCTTCT CTTAATTAT TCTTCCTTTA
ACCGGAACCG TGCTGGTTCA GCTAACCGGT CTAACGTTCG ATACGTTCTC TGAGCTTTGG
TCTAACCAGG CGGTTCAACT CGACACGGCG ACGAGACTTA CCTGCTTGGT TTTCCTCTCC
TTCGTTTTGA CCCTCTACGT GGCTAACCGG TCTAAACCGG TTTACCTAGT GGATTTCTCC
TGCTACAAAC CGGAAGACGA GCGTAAAATA TCAGTAGATT CGTTCTTGAC GATGACTGAG
GAAAATGGAT CATTCACCGA TGACACGGTT CAGTTCCAGC AAAGAATCTC GAACCGGGCC
GGTTTGGGAG ACGAGACGTA TCTGCCACGT GGCATAACTT CAACGCCCCC GAAGCTAAAT
ATGTCAGAGG CACGTGCCGA AGCTGAAGCC GTTATGTTTG GAGCCTTAGA TTCCCTCTTC
GAGAAAACCG GAATTAAACC GGCCGAAGTC GGAATCTTGA TAGTAAACTG CAGCTTATTC
AATCCGACGC CGTCTCTATC AGCGATGATC GTGAACCATT ACAAGATGAG AGAAGACATC
AAAAGTTACA ACCTCGGAGG AATGGGTTGC TCCGCCGGAT TAATCTCAAT CGATCTCGCT
AACAATCTCC TCAAAGCAAA CCCTAATTCT TACGCTGTCG TGGTAAGCAC GGAAAACATA
ACCCTAAACT GTACTTCGG AAATGACCGG TCAATGCTCC TCTGCAACTG CATCTTCCGA
ATGGCGGAG CTGCGATTCT CCTCTCTAAC CGCCGTCAAG ACCGGAAGAA GTCAAAGTAC
TCGCTGGTCA ACGTCGTTCG AACACATAAA GGATCAGACG ACAAGAACTA CAATTGCGTG
TACCAGAAGG AAGACGAGAG AGGAACAATC GGTGTCTCTT TAGCTAGAGA GCTCATGTCT
GTCGCCGGAG ACGCTCTGAA AACAAACATC ACGACTTTAG GACCGATGGT TCTTCCATTG
TCAGAGCAGT TGATGTTCTT GATTTCCTTG GTCAAAAGGA AGATGTTCAA GTTAAAAGTT
AAACCGGTAT TTCCGGATTT CAAGCTAGCT TTCGAGCATT TCTGTATTCA CGCAGGAGGT
AGAGCGGGTC TAGACGAAGT GCAGAAGAAT CTTGATCTCA AAGATTGGCA CATGGAACCT
TCTAGAATGA CTTTGCACAG ATTTGGTAAC ACTTCGAGTA GCTCGCTTTG GTATGAGATG
GCTTATACCG AAGCTAAGGG TCGGGTTAAA GCTGGTGACC GACTTTGGCA GATTGCGTTT
GGATCGGGTT TCAAGTGTAA TAGTGCGGTT TGGAAAGCGT TACGACCGGT TTCGACGGAG
GAGATGACCG GTAATGCTTG GGCTGGTTCG ATTGATCAAT ATCCGGTTAA AGTTGTGCAA
                           EL1
                          FIG. 3
```

FIG. 4

EL1 sequence
Molecular Weight 58379.00 Daltons
520 Amino Acids
62 Strongly Basic(+) Amino Acids (K,R)
52 Strongly Acidic(-) Amino Acids (D,E)
187 Hydrophobic Amino Acids (A,I,L,F,W,V)
144 Polar Amino Acids (N,C,Q,S,T,Y)
8.784 Isoelectric Point
10.804 Charge at PH 7.0

MDRERLTAEM AFRDSSSAVI RIRRRLPDLL TSVKLKYVKL GLHNSCNVTT ILFFLIILPL
TGTVLVQLTG LTFDTFSELW SNQAVQLDTA TRLTCLVFLS FVLTLYVANR SKPVYLVDFS
CYKPEDERKI SVDSFLTMTE ENGSFTDDTV QFQQRISNRA GLGDETYLPR GITSTPPKLN
MSEARAEAEA VMFGALDSLF EKTGIKPAEV GILIVNCSLF NPTPSLSAMI VNHYKMREDI
KSYNLGGMGC SAGLISIDLA NNLLKANPNS YAVVVSTENI TLNWYFGNDR SMLLCNCIFR
MGGAAILLSN RRQDRKKSKY SLVNVVRTHK GSDDKNYNCV YQKEDERGTI GVSLARELMS
VAGDALKTNI TTLGPMVLPL SEQLMFLISL VKRKMFKLKV KPYIPDFKLA FEHFCIHAGG
RAVLDEVQKN LDLKDWHMEP SRMTLHRFGN TSSSSLWYEM AYTEAKGRVK AGDRLWQIAF
GSGFKCNSAV WKALRPVSTE EMTGNAWAGS IDQYPVKVVQ

```
EL2    1479 bases

ATGGATTACC CCATGAAGAA GGTAAAAATC TTTTTCAACT ACCTCATGGC GCATCGCTTC
AAGCTCTGCT TCTTACCATT AATGGTTGCT ATAGCCGTGG AGGCGTCTCG TCTTTCCACA    120
CAAGATCTCC AAAACTTTTA CCTCTACTTA CAAAACAACC ACACATCTCT AACCATGTTC
TTCCTTTACC TCGCTCTCGG GTCGACTCTT TACCTCATGA CCCGGCCCAA ACCCGTTTAT    240
CTCGTTGACT TTAGCTGCTA CCTCCCACCG TCGCATCTCA AAGCCAGCAC CCAGAGGATC
ATGCAACACG TAAGGCTTGT ACGAGAAGCA GGCGCGTGGA AGCAAGAGTC CGATTACTTG    360
ATGGACTTCT GCGAGAAGAT TCTAGAACGT TCCGGTCTAG GCCAAGAGAC GTACGTACCC
GAAGGTCTTC AAACTTTGCC ACTACAACAG AATTTGGCTG TATCACGTAT AGAGACGGAG    480
GAAGTTATTA TTGGTGCGGT CGATAATCTG TTTCGCAACA CGGGAATAAG CCCTAGTGAT
ATAGGTATAT AGTTTAAACT TAGGGATAAT ATAAAGAGCT CACCTTCGCT ATCAAGTATC    600
TTAGTAGCTG GAGTCATCGC TATCGATGCG GCTAAGAGCT TGAATCTTGG TGGGATGGGG
TGTAGCGCTG GAGTCATCGC TATCGATGCG GCTAAGAGCT TGTTACAAGT TCATAGAAAC    720
ACTTATGCTC TTGTGGTGAG CACGGAGAAC ATCACTCAAA ACTTGTACAT GGGTAACAAC
AAATCAATGT TGGTTACAAA CTGTTTGTTC CGTATAGGTG TACGAGCTTG TTTGCTTTCT    840
AACCGGTCTA TAGATCGTAA ACGCGCAAAA ACGCGCAAAA TACGAGCTTG GCGGGTCCAT
ACCGGAGCAG ATGACCGATC CTATGAATGT GCAACTACAA AAGAGGATGA AGATGGCATA    960
GTTGGGGTTT CCTTGTCAAA GAATCTACCA ATGGTAGCTG CAAGAACCCT AAAGATCAAT
ATCGCAACTT TGGGTCCGCT TGTTCTTCCC ATAAGCGAGA AGTTTCACTT CTTTGTGAGG    1080
TTCGTTAAAA AGAAGTTTCT CAACCCCAAG CTAAAGCATT ACATTCCGGA TTTCAAGCTC
GCATTCGAGC ATTTCTGTAT CCATGCGGGT GGTAGAGCGC TAATTGATGA GATGGAGAAG    1200
AATCTTCATC TAACTCCACT AGACGTTGAG GCTTCAGAAA TGACATTACA CAGGTTTGGT
AATACCTCTT CGAGCTCCAT TGGTACGAG GCAGATTGCG TTGGCTTACA CAGAAGCCAA AGGAAGGATG    1320
ACGAAAGGAG ATAGGATTTG GCAGATTGCG CGTCAAGCCT GTTTAAGTG TAATAGTTCA
GTTGGGTGG CTCTTCGTAA CGTCAAGCCT CGATATAGAT ATCCTTGGGA ACAGTGTCTA    1440
CACAAATATC CAGTTGAGAT TTAAAGAG

EL2 protein sequence
Molecular Weight 55799.30 Daltons
493 Amino Acids
55 Strongly Basic(+) Amino Acids (K,R)
46 Strongly Acidic(-) Amino Acids (D,E)
181 Hydrophobic Amino Acids (A,I,L,F,W,V)
134 Polar Amino Acids (N,C,Q,S,T,Y)
8.756 Isoelectric Point
10.995 Charge at PH 7.0

```
MDYPMKKVKI FFNYLMAHRF KLCFLPLMVA IAVEASRLST QDLQNFYLYL QNNHTSLTMF FLYLALGSTL
YLMTRPKPVY LVDFSCYLPP SHLKASTQRI MQHVRLVREA GAWKQESDYL MDFCEKILER SGLGQETYVP
EGLQTLPLQQ NLAVSRIETE EVIIGAVDNL FRNTGISPSD IGILVVNSST FNPTPSLSSI LVNKFKLRDN
IKSLNLGGMG CSAGVIAIDA AKSLLQVHRN TYALVVSTEN KSMLVTNCLF RIGGAAILLS
NRSIDRKRAK YELVHTVRVH TGADDRSYEC ATQEEDEDGI VGVSLSKNLP MVAARTLKIN IATLGPLVLP
ISEKFHFFVR FVKKKFLNPK LKHYIPDFKL AFEHFCIHAG GRALIDEMEK NLHLTPLDVE ASRMTLHRFG
NTSSSSIWYE LAYTEAKGRM TKGDRIWQIA LGSGFKCNSS VWVALRNVKP STNNPWEQCL HKYPVEIDID
LKE
```

EL3    1512 bases

```
CTACGTCAGG GTAGAACAAA GAGTAAACAC TTAAGCAAAA CAATTGTCCC TACTCTTAGG TTATCTCCAA
TGAAGAACTT AAAGATGGTT TTCTTCAAGA TCCTCTTTAT CTCTTTAATG GCAGGATTAG CCATGAAAGG
ATCTAAGATC AACGTAGAAG ATCTCCAAAA GTTCTCCCTC CACCATACAC AGAACAACCT CCAAACCATA
AGCCTTCTAT TGTTTCTTGT CGTTTTTGTG TGGATCCTCT ACATGTTAAC CCGACCTAAA CCCGTTTACC
TTGTTGATTT CTCCTGCTAC CTTCCACCGT CGCATCTCAA GGTCAGTATC CAAACCCTAA TGGGACACGC
AAGACGTGCA AGAGAAGCAG GCATGTGTTG GAAGAACAAA GAGAGCGACC ATTTAGTTGA CTTCCAGGAG
AAGATTCTTG AACGTTCCGG TCTTGGTCAA GAAACCTACA TCCCCGAGGG TCTTCAGTGC TTCCCACTTC
AGCAAGGCAT GGGTGCTTCA CGTAAAGAGA CGGAAGAAGT AATCTTCGGA GCTCTTGACA ATCTTTTTCG
CAACACCGGT GTAAAACCTG ATGATATCGG TATATTGGTG GTGAATTCTA GCACGTTTAA TCCAACTCCA
TCACTCGCCT CCATGATTGT GAACAAGTAC AAACTCAGAG ACAACATCAA GAGTTTGAAT CTTGGAGGGA
TGGGTTGCAG TGCCGGAGTT ATAGCTGTTG ATGTCGCTAA GGGATTACTA CAAGTTACTA GAACACTTA
TGCTATTGTA GTAAGCACAG AGAACATCAC TCAGAACTTA GCGGTTCTGC TTTCAAACAG ATCTAGAGAC
ACAAACTGTT TGTTCCGCGT TGGTGGTGCT TCCATACCGG AGTTACCTTG ATCAGATGAT AGGTCGTTCG
CCAAATACGA GCTTGTTCAC ACCGTACGGA GTTACCTTGG ACTTACCTTG ATCAGATGAT AGGTCGTTCG
ACAAGAAGAG GATGAAGATG GTATAATTGG AGTTACCTTG TACCTATGGT AGGAAGCTA TACCTATGGT
ACTCTTAAGA TAAATATCGC AACTTTGGGT TATTTCAAGC CTGGTGGAAG AGCTCTAATA CTACACAGT
TTACTTTTGT CAAGAAGAAG TATTTCAAGC CTGGTGGAAG AGCTCTAATA CTACACAGT GGATGAAGGA
TGAGCATTTC TGTATCCACG CTGGTGGAAG AGCTCTAATA CTACACAGT GGATGAAGGA AGGAGATAGG
CCGTTACACG TAGAGGCGTC AAGAATGACA AGAATGACA TTGGTAACAC AGGAGATAGG AGGAGATAGG
ACGAGTTAGC TTATACAGAA GCTAAAGGAA GTTCAGTATG GTTGGCTCTG CGAGACGTTA TTGCTTTGGG
GTCAGGTTTT AAGTGTAACA GTTCAGTACA ATATCCGGTT CGAGACGTTA AGCCTTCAGC TAACAGTCCA
TGGGAAGACT GTATGGATAG ATATCCGGTT GAGATTGATA TT
```

FIG. 7

EL3 protein sequence
Molecular Weight 56801.10 Daltons
504 Amino Acids
66 Strongly Basic(+) Amino Acids (K,R)
48 Strongly Acidic(-) Amino Acids (D,E)
183 Hydrophobic Amino Acids (A,I,L,F,W,V)
127 Polar Amino Acids (N,C,Q,S,T,Y)
9.315 Isoelectric Point
19.797 Charge at PH 7.0

```
LRQGRTKSKH LSKTICPTLR LSPMKNLKMV FFKILFISLM AGLAMKGSKI NVEDLQKFSL HHTQNNLQTI
SLLFLVVFV  WILYMLTRPK PVYLVDFSCY LPPSHLKVSI QTLMGHARRA REAGMCWKNK ESDHLVDFQE
KILERSGLGQ ETYIPEGLQC FPLQQGMGAS RKETEEVIFG ALDNLFRNTG VKPDDIGILV VNSSTFNPTP
SLASMIVNKY KLRDNIKSLN LGGMGCSAGV IAVDVAKGLL QVHRNTYAIV VSTENITQNL YLGKNKSMLV
TNCLFRVGGA AVLLSNRSRD RNRAKYELVH TVRIHTGSDD RSFECATQEE DEDGIIGVTL TKNLPMVAAR
TLKINIATLG PLVLPLKEKL AFFITFVKKK YFKPELRNYT PDFKLAFEHF CIHAGGRALI DELEKNLKLS
PLHVEASRMT LHRFGNTSSS SIWYELAYTE AKGRMKEGDR IWQIALGSSGF KCNSSVWVAL RDVKPSANSP
WEDCMDRYPV EIDI
```

```
EL4 cDNA           1650 bases
ATGGGTAGAT CCAACGAGCA AGATCTGCTC TCTACCGAGA TCGTTAATCG TGGGATCGAA CCATCCGGTC
CTAACGCCGG CTCACCAACG TTCTCGGTTA GGGTCAGGAG ACGTTTGCCT GATTTCTTC AGTCGGTGAA
CTTGAAGTAC GTGAAACTTG GTTACCACTA CCTCATAAAC CATGCGGTTT ATTTGGCGAC CATACCGTT
CTTGTGCTGG TTTTAGTGC TGAGGTTGGG AGTTTAAGCA GAGAAGAAG TTGGAAGAAG CTTTGGACT
ATGATCTTGC AACTGTTATC GGATTCTTCG GTGTCTTTGT TTTAACCGCT TGTGTCTACT TCATGTCTCG
TCCTCGCTCT GTTTATCTTA TTGATTTCGC TTGTTACAAG CCCTCCGATG AACACAAGGT GACAAAAGAA
GAGTTCATAG AACTAGCGAG AAAATCAGG AAGTTCGACG CGGTTTCAAG AAGAGGATCT
TACAAGCCTC AGCCATAGGC GACGAGACAT ACGTCCCAAG TCATCAGAAA ACATAACAAC
GATGAAAGAA GGTCGTGAAG AAGCCTCTAC AGTGATCTTT GGAGCACTAG ACGAACTCTT CGAGAAGACA
CGTGTAAAAC CTAAAGACGT TGGTGTCCTT GTAGCATTTT CAACCCGACA AACCTTGGAG CCGTCGTTGT
CCGCAATGGT GATAAACCAT TACAAGATGA GTGGTTAACT ACTTAGTTAC AACCTTGGAG GGATGGGATG
TTCGGCTGGA ATCATAGCTA TTGATCTTGC TCGTGACATG CTTCAGTGTA ACCCTAATAG TTATGCTGTT
GTGTGCTGAGTA CTGAGATGGT TGGGTATAAT TGGTACGTGG GAAGTGACAA GTCAATGGTT ATACCTAATT
GTTTCTTTAG GATGGGTTGT TCTGCCGTTA TGCTCTCTAA CCGTCGTCGT GACTTTCGCC ATGCTAAGTA
CCGTCTCGAG CACATTGTCC GAACTCATAA GGCTGCTGAC GACCGTAGCT TCAGGAGTGT GTACCAGGAA
GAAGATGAAC AAGGATTCAA GGGGTTGAAG ATAAGTAGAG ACTTAATGGA AGTTGGAGGT GAAGCTCTCA
AGACAAACAT CACTACCTTA GGTCCCTCTG CTCCGAGCAG CTCTCTACTTC TTGCTGCTTT
GGTCCGCCGA ACATTCTCAC CTGCTGCCAA AACGTCCACA ACCACTTCCT CCCGACTAC CGCCACCGCA
AAAACCAATG GAATCAAGTC TTCCTCTTCC GATCTGTCCA AGCCATACAT CCCGACTAC AAGCTCGCCT
TCGAGCATT TTGCTTCCAC GCGGCAAGCA AAGTAGTGCT TGAAGAGCTT CAAAAGAATC TAGGCTTGAG
TGAAGAGAAT ATGGAGGCTT CTAGGATGAC ACTTCACAGG TTTGGAAACA CTTCTAGCAG TGGAATCTGG
TATGAGTTGG CTTACATGGA GGCCAAGGAA AGTAGTTCGTA AGTGTTCGTA GGTTGGCAG ATCGCTTTCG
GTTCTGGTTT TAAGTGTAAC AGTGTGGTGT GGAAGGCAAT ACTTCACAGG GAGGCGATAG CCAGAGAACAA
TCCTTGGGTG GATTGCATCA ACCGTTACCC TGTGCCTCTC                    GAGGAAGGTG AAGAAGCCAA
```

FIG. 9

EL4 protein sequence
Molecular Weight 61953.80 Daltons
550 Amino Acids
71 Strongly Basic(+) Amino Acids (K,R)
58 Strongly Acidic(-) Amino Acids (D,E)
191 Hydrophobic Amino Acids (A,I,L,F,W,V)
147 Polar Amino Acids (N,C,Q,S,T,Y)
9.036 Isoelectric Point
14.349 Charge at PH 7.0

MGRSNEQDLL STEIVNRGIE PSGPNAGSPT FSVRVRRRLP DFLQSVNLKY VKLGYHYLIN HAVYLATIPV
LVLVFSAEVG SLSREEIWKK LWDYDLATVI GFFGVFVLTA CVYFMSRPRS VYLIDFACYK PSDEHKVTKE
EFIELARKSG KFDEETLGFK KRILQASGIG DETYVPRSIS SSENITTMKE GREEASTVIF GALDELFEKT
RVKPKDVGVL VVNCSIFNPT PSLSAMVINH YKMRGNILSY NLGGMGCSAG IIAIDLARDM LQSNPNSYAV
VVSTEMVGYN WYVGSDKSMV IPNCFFRMGC SAVMLSNRRR DFRHAKYRLE HIVRTHKAAD DRSFRSVYQE
EDEQGFKGLK ISRDLMEVGG EALKTNITTL GPLVLPFSEQ LFFAALVRR TFSPAAKTST TTSFSTSATA
KTNGIKSSSS DLSKPYIPDY KLAFEHFCFH AASKVVLEEL QKNLGLSEEN MEASRMTLHR FGNTSSSGIW
YELAYMEAKE SVRRGDRVWQ IAFGSGFKCN SVVWKAMRKV KKPTRNNPWV DCINRYPVPL

```
EL5 cDNA       1611 bases
TCGAGCTACG TCAGGGCTTT TATATGCACA AATTCTCATA AAGTTTTCAA TTTTATTCCA TTTTTCTCGG
AAGCCATGGA AGCTGCTAAT GAGCCTGTTA TACAAAGCGT CAACATGAAA CGTACAGATC CGAACAGAGA ACAACGAAAG
ACGAAAGCTT CCTAATTTCT TACAAAGCGT TTAATGGCGG TTTAGTCAC AGAGATCTCT TAGGTTATCA TTACCTCATT
ACTCATCTCT TCAAGCTCTG TTTGGTTCCA TCCAATACAA TCTCGTTGCT AGAGATCTCT CGATTAACAA
CAGACGATCT TTACCAGATT TGGCTTCATC GAGTCGTCCC AGATCTGTTT TTCATCTTTC TCTCTGCTTT
AGCTATCTTT GGCTCCACCG TTTACATCAT TCAGGTTAAG TATCAGAAGT TTATGGATCA ATCTCGTTGA TTACTCTTGT
TATCTTCCTC CGGAGAGTCT TCAGGTTAAG AGATTCTTGA TTTCAGAGGA TTCTAAGTTG ATTGAAGATT
TCAATGAGTC ATCTTTAGAG TTTCAGAGGA AGATTCTTGA ACGTTCTGGT TTAGGAGAAG AGACTTATCT
CCCTGAAGCT TTACATTGTA TCCCCTCGAG GCCTACGATG AATACCAAGA ATGGCGGCTC GTGAGGAATC TGAGCAGGTA
ATGTTTGGTG CTCTTTCGAG GCTTTTCGAG CGTTGTCAGC TTAACCCTAG TTAACCTAG TATGATTGTT GGATATTGGT GTGTTGGTTG
TGAATTGTAG CTTGTTTAAT CCTACACCTT GGGGTGTAGT TATGATTGTT TATGATTGTA AACAAGTATA AGCTTAGCTAAA
GAATGTTAAG AGTTTTAACC TTGGTGGAAT GCTGGTGTGG TTAGTACTGA TCTCTATCGA CAGAATTGGT
GATATGTTGC AAGTTCATAG GAATACTTAT CGAATTGTTT GTTCGTGTT GGTGGTTCGG CGATTTTGTT
ATTTGGGAA TAAGAAGGCT ATGTTGATTC GTAGACGGTC CTTGTTCATA CCGTTAGGAC TCATAAAGGA
GTCGAACAAG GGGAAAGATC GTAGACGGTC CTGTGTTTAC ATGATAAATGG GAAGACCGGG GTTCGTTGT
GCTGTTGAGA AGGCTTTCAA CTGTGTTTAC GCTGGGGAAG GAATATCACT ACTTTAGGTC CTTTGGTTCT
CGAAAGATCT TATGGCTATA GCTGGGGAAG CTCTTAAGGC ACTTTAGGTC TGTTTAACTC GAAGCTGAAG
TCCTATAAGT GAGCAGATTC TGTTTTTCAT GACTTTGGTT ACGAAGAAAC TGGTGGTAGA GCTGTGATTG
CCGTATATTC CGGATTCAA GCTTGCGTTT GATCATTTCT GTATCCATGC AGAATGACAC TGCACAGATT
ATGAGCTTGA GAAGAATCTG CAGCTTTCGC AGACTCATGT CGAGGCATCC CTAAAGGTAG GATGAAGAAA
TGGAAACACT TCTTCGAGCT CGATTTGGTA TGAACTGGCT TACATAGAGG TGCAGTTTGG GTGCTCTAA
GAAACCGGG TTTGGCAGAT TGCTTTTGGA AGTGGGTTTA AGTGTAACAG CATCGACCGA TATCCGGTTA AGCTCGACTT
ACAATGTCAA GCCTTCGGTT AGTAGTCCGT GGGAACACTG GGGAACACTG CATCGACCGA
C
```

FIG. 11

EL5 protein sequence
Molecular Weight 60874.60 Daltons
537 Amino Acids
63 Strongly Basic(+) Amino Acids (K,R)
47 Strongly Acidic(-) Amino Acids (D,E)
198 Hydrophobic Amino Acids (A,I,L,F,W,V)
148 Polar Amino Acids (N,C,Q,S,T,Y)
9.107 Isoelectric Point
17.930 Charge at PH 7.0

```
SSYVRAFICT NSHKVFNFIP FFSEAMEAAN EPVNGGSVQI RTENNERRKL PNFLQSVNMK YVKLGYHYLI
THLFKLCLVP LMAVLVTEIS RLITTDDLYQI WLHLQYNLVA FIFLSALAIF LGEETYLPEA GSTVYIMSRP RSVYLVDYSC
YLPPESLQVK YQKFMDHSKL IEDFNESSLE FQRKILERSG NKYKLRGNVK LHCIPPRPTM MAAREESEQV
MFGALDKLFE NTKINPRDIG VLVVNCSLFN PTPSLSAMIV MLIPNCLFRV SFNLGGMGCS AGVISIDLAK
DMLQVHRNTY AVVVSTENIT QNWYFGNKKA VSLSKDLMAI AGEALKANIT GGSAILLSNK GKDRRRSKYK LVHTVRTHKG
AVEKAFNCVY QEQDDNGKTG DHFCIHAGGR AVIDELEKNL QLSQTHVEAS TLGPLVLPIS EQILFFMTLV TKKLFNSKLK
PYIPDFKLAF SGFKCNSAVW VALNNVKPSV SSPWEHCIDR RMTLHRFGNT SSSSIWYELA YIEAKGRMKK
GNRVWQIAFG YPVKLDF
```

```
EL6        1502 bases
TCTCCGACGATGCCTCAGGCACCGATGCCAGAGTTCTCTAGCTCGGTGAAGCTCAAGTACGTGAAACTTGGTTACCAA
TATTGGTTAACCATTTCTTGAGTTTTCTTTTGATCCGATCATGGCTATTGTGCCGTTGAGCTTCTTCGATGGGT
CCTGAAGAGATCCTTAATGTTTGGAATTCACTCCAGTTTGACCTAGTTCAGTTCTTCCTTCTTTGTCATC
TTCATCTCCACTGTTTACTTCAGTCCAAGCCACGACCATTCTCGTTGACTATTCTGTTACAAGCCACCTGTC
ACGTGTCGTGTCCCTTCGCAACTTTCATGGAACACTCTCGTTGATCCTCAAGGACAAGCCTAAGAGCGTCGAGTTC
CAAATGAGAATCCTTGAACGTTCTGGCCTCGGTGAGGAGACTTGTCTCCCTCCGGCTATTCATTATATTCCCACA
CCAACCATGACGCGGCTAGAAGCGAGGCTCAGATGGTTATCTGCTCTCTTTTCTCTCGGGGATGGGCTGCAGGCCATGATCGT
CTTAAACCTAAAGACGTCGACATCCTTATCGTCAAGAGTAATATCAAGAGCTTCAATCTTTCGGGATGGGCTGCAGCGCTGATCTCA
GTTGATCTAGCCCGCGACTTGCTCCAAGTTCATCCAAGTTCCAATTCAAATGCAATGAAATGCTCAGCACGAGATCATAACGCCT
AATTACTATCAAGGCAACGAGAGCCATGTTGTTACCCAATACAAGAGCTTTCCCACCACTTGTGTCCATGGGTGCGGCAGCCATAACATG
TCAAACCGCCGGTCTGTCTACGAACAGGAAGAAGACACGTTGGCATCCATACCGCGTCAGAATTCAAGCTGCCTTCGAA
AAGTCTTTCTACTGTGTCTACGAACAGGAAGAAGACACGTTGGCATCCATACCGCGTCAGAATTCAAGCTGCCTTCGAA
ATCGCCGGTGAAGCCCTCAAGCACTAAGCAGTAAAATCCACCACAGTAGTCCTTTGGTCGTCACCGCGTCAGAATTCAAGCTGCCTTCGAA
CTCACGTCCCTAATGCATTCACGCGCAGGAGGACTACAGAGGCAGAGACGTCGTTTGGTAACACGTCATCTTCGCGTTTATGGTAGTTAGCTACATCGAG
CACTTTTGCATTGCATTCACGCGCAGGAGGACTACAGAGGCAGAGACGTCGTTTGGTAACACGTCATCTTCGCGTTTATGGTAGTTAGCTACATCGAG
GAGGCCTCAAGAATGACAGAATGAGGAGGCTACGATTAAGACACCTAAGGACGGACCATGGTCCGATTGTATCGACCGTTACCCTGTCTTTATT
CCCGAAGTTGTCAAACTCTA
```

FIG. 13

EL6 protein sequence
Molecular Weight 56687.90 Daltons
500 Amino Acids
59 Strongly Basic(+) Amino Acids (K,R)
46 Strongly Acidic(-) Amino Acids (D,E)
182 Hydrophobic Amino Acids (A,I,L,F,W,V)
127 Polar Amino Acids (N,C,Q,S,T,Y)
8.909 Isoelectric Point
14.567 Charge at PH 7.0

```
SPTMPQAPMP EFSSSVKLKY VKLGYQYLVN HFLSFLLIPI MAIVAVELLR MGPEEILNVW NSLQFDLVQV
LCSSFFVIFI STVYFMSKPR TIYLVDYSCY KPPVTCRVPF ATFMEHSRLI LKDKPKSVEF QMRILERSGL
GEETCLPPAI HYIPPTPTMD AARSEAQMVI FEAMDDLFKK TGLKPKDVDI LIVNCSLFSP TPSLSAMVIN
KYKLRSNIKS FNLSGMGCSA GLISVDLARD LLQVHPNSNA IIVSTEIITP NYYQGNERAM LLPNCLFRMG
AAAIHMSNRR SDRWRAKYKL SHLVRTHRGA DDKSFYCVYE QEDKEGHVGI NLSKDLMAIA GEALKANITT
IGPLVLPASE QLLFLTSLIG RKIFNPKWKP YIPDFKLAFE HFCIHAGGRA VIDELQKNLQ LSGEHVEASR
MTLHRFGNTS SSSLWYELSY IESKGRMRRG DRVWQIAFGS GFKCNSAVWK CNRTIKTPKD GPWSDCIDRY
PVFIPEVVKL
```

EL7   1548 bases
ATGGACGGTGCCGGAGAATCACGACTCGGTGGTGGTGATGGTGGTGATGGTTCTGTTGGAGTTCAGATCCGACAAACA
CGGATGCTACCGGATTTCTCCAGAGCGTGAATCTCAAGTATGTGAAATTAGGTTACCATTACTTAATCTCAAATCTC
TTGACTCTCTGTTTATTCCCTCTCGCCGTTGTTATCCGTGAAGCCTCTCAGATGAACCCAGATGATCTCAAACAG
CTCTGGATCCATCTACAATACAAATCTGTTAGTATCATCTGTTGTTGTTCTCTTCTGATTCTAGTCTCGGTTAACGCtCCTTAC
GTTATGACCCGACCTAGAACATTCTAGAACATTCACCGGAACTTCGATGACTCTGCTCTGAGTTTCAACGCAAGATCCTTGAG
GCTCGGTTCATGGAAGACACTTATGTCCCTGAAGCTATGCATTATGTTCCACCGAGAATTTCAATGGCTGCTGCT
CGTTCTGGTTTAGGGAAGACACTTATGTCCCTGAAGCTATGCATTATGTTCCACCGAGAATTTCAATGGCTGCTGCT
AGAGAAGAAGCTGAACAAGTCATGTTTGTGCTTTAGATAACCTTTTCGCTAACACTAATGTGAAACCAAAGGATATT
GAATCCTTGTTGTGAATTGTAGTTCTCTTTAATCCAACTCCTTCGTTATCGCACGCGGAGTTATCGCTGTGATCTTGCTAAAGAC
AGAGGTAACATTAGAAGCTACATCTAGGCGGTATGGCGGTGTGTTTCTACTGAGAACATTACTCAGAATTGGTATTTGGTAAC
ATGTTGTTGGTACATAGAACTGAACACTTATGCGGTTGTGTTCGAGTTGGTGGCCTCTGCGGTTTGCTATCGAACAAGTCGAGGGAC
AAGAAATCGATGTTGATACCGATGATAAAGCTTTCCGTTGTGTT
AAGAGACGGTCTAAGTAGCAGGATGATACAGGGAGAACCGGGGTTTCGTTGTCGAACAAGATCTAAATGGCGATTGCAGGGGAAACTCTC
TATCAAGACCAGGATACCACTCATTGGTCCTCTTGTTCTACCGATAAGTGAGCAGATTTCTCTTTATGACTCTAGTTGTG
AAAACCAATATCACTACATTGGGTCCTCTTGTTCTACCGATAAGTGAGCAGATTTCTCTTTATGACTCTAGTTGTG
AAGAAGCTCTTAACGTAAAGTGAAACGTAAAGTGAAACGTATATCCCGGATTTCAAACTTGCTTTCAACCAGTTCACCATTGCTGTTACTCACAGTTCCATGCT
GGTGAAGAGCTGTGATGATCGATGAGTGAGTTAGAGAGAATCTGCAGCTTCACCAGTTGCTTACATTGGCTTACATTGGTATGAATTGAAGCGAAGGAAGGATGACT
CTTCATCGATTGTGTTTGGCAAATCGCGTTCGAGCTACATCTGGAAGTGGATTTAAATGTAATAGCGCGATTGGGAAGCATTAAGGCAT
AGAGGTAATCGTGTTTGGCAAATCAGTCCTGGGAAGATTGTATTGACACAAGTATCCGGTAACTTTAAGTTAT
GTGAAACCTTCGAACAGTCCTTGGGAAGATTGTATTGACAAGTATCCGGTAACTTTAAGTTAT

EL7 protein sequence
Molecular Weight 57848.80 Daltons
516 Amino Acids
59 Strongly Basic(+) Amino Acids (K,R)
48 Strongly Acidic(-) Amino Acids (D,E)
189 Hydrophobic Amino Acids (A,I,L,F,W,V)
131 Polar Amino Acids (N,C,Q,S,T,Y)
8.872 Isoelectric Point
12.792 Charge at PH 7.0

```
MDGAGESRLG GDGGGDGSVG VQIRQTRMLP DFLQSVNLKY VKLGYHYLIS NLLTLCLFPL AVVISVEASQ
MNPDDLKQLW IHLQYNLVSI IICSAILVFG LTVYVMTRPR PVYLVDFSCY LPPDHLKAPY ARFMEHSRLT
GDFDDSALEF QRKILERSGL GEDTYVPEAM HYVPPRISMA AAREEAEQVM FGALDNLFAN TNVKPKDIGI
LVVNCSLFNP TPSLSAMIVN KYKLRGNIRS YNLGGMGCSA GVIAVDLAKD MLLVHRNTYA VVVSTENITQ
NWYFGNKKSM LIPNCLFRVG GSAVLLSNKS RDKRRSKYRL VHVVRTHRGA DDKAFRCVYQ EQDDTGRTGV
SLSKDLMAIA GETLKTNITT LGPLVLPISE QILFFMTLVV KKLFNGKVKP YIPDFKLAFE HFCIHAGGRA
VIDELEKNLQ LSPVHVEASR MTLHRFGNTS SSSIWYELAY IEAKGRMRRG NRVWQIAFGS GFKCNSAIWE
ALRHVKPSNN SPWEDCIDKY PVTLSY
```

FATTY ACID ELONGASES

FIELD OF THE INVENTION

This invention relates to fatty acid elongase complexes and nucleic acids encoding elongase proteins. More particularly, the invention relates to nucleic acids encoding β-keto acyl synthase proteins that are effective for producing very long chain fatty acids, polypeptides produced from such nucleic acids and transgenic plants expressing such nucleic acids.

BACKGROUND OF THE INVENTION

Plants are known to synthesize very long chain fatty acids (VLCFAs). VLCFAs are saturated or unsaturated monocarboxylic acids with an unbranched even-numbered carbon chain that is greater than 18 carbons in length. Many VLCFAs are 20–32 carbons in length, but VLCFAs can be up to 60 carbons in length. Important VLCFAs include erucic acid (22:1, i.e., a 22 carbon chain with one double bond), nervonic acid (24:1), behenic acid (22:0), and arachidic acid (20:0).

Plant seeds accumulate mostly 16- and 18-carbon fatty acids. VLCFAs are not desirable in edible oils. Oilseeds of the Crucifereae (e.g., rapeseed) and a few other plants, however, accumulate C20 and C22 fatty acids (FAs). Although plant breeders have developed rapeseed lines that have low levels of VLCFAs for edible oil purposes, even lower levels would be desirable. On the other hand, vegetable oils having elevated levels of VLCFAs are desirable for certain industrial uses, including uses as lubricants, fuels and as a feedstock for plastics, pharmaceuticals and cosmetics.

The biosynthesis of saturated fatty acids up to an 18-carbon chain occurs in the chloroplast. C2 units from acyl thioesters are linked sequentially, beginning with the condensation of acetyl Coenzyme A (CoA) and malonyl acyl carrier protein (ACP) to form a C4 acyl fatty acid. This condensation reaction is catalyzed by a β-ketoacyl synthase III (KASIII). β-ketoacyl moieties are also referred to as 3-ketoacyl moieties.

The enzyme β-ketoacyl synthase I (KASI) is involved in the addition of C2 groups to form the C6 to C16 saturated fatty acids. KASI catalyzes the stepwise condensation of a fatty acyl moiety (C4 to C14) with malonyl-ACP to produce a 3-ketoacyl-ACP product that is 2 carbons longer than the substrate. The last condensation reaction in the chloroplast, converting C16 to C18, is catalyzed by β-ketoacyl synthase II (KASII).

Each elongation cycle involves three additional enzymatic steps in addition to the condensation reaction as discussed above. Briefly, the β-ketoacyl condensation product is reduced to β-hydroxyacyl-ACP, dehydrated to the enoyl-ACP, and finally reduced to a fully reduced acyl-ACP. The fully reduced fatty acyl-ACP reaction product then serves as the substrate for the next cycle of elongation.

The C18 saturated fatty acid (stearic acid, 18:0) can be transported out of the chloroplast and converted to the monounsaturate C18:1 (oleic acid), and the polyunsaturates C18:2 (linoleic acid) and C18:3 (α-linolenic acid). C18:0 and C18:1 can also be elongated outside the chloroplast to form VLCFAs. The formation of VLCFAs involves the sequential condensation of two carbon groups from malonyl CoA with a C18:0 or C18:1 fatty acid substrate. Elongation of fatty acids longer than 18 carbons depends on the activity of a fatty acid elongase complex to carry out four separate enzyme reactions similar to those described above for fatty acid synthesis in the chloroplast. Fehling, Biochem. Biophys. Acta 1082:239–246 (1991). In plants, elongase complexes are distinct from fatty acid synthases since elongases are extraplastidial and membrane bound.

Mutations have been identified in an Arabidopsis gene associated with fatty acid elongation. This gene, designated the FAE1 gene, is involved in the condensation step of an elongation cycle. See, WO 96/13582, incorporated herein by reference. Plants carrying a mutation in FAE1 have significant decreases in the levels of VLCFAs in seeds. Genes associated with wax biosynthesis in jojoba have also been cloned and sequenced (WO 95/15387, incorporated herein by reference).

Very long chain fatty acids are key components of many biologically important compounds in animals, plants, and microorganisms. For example, in animals, the VLCFA arachidonic acid is a precursor to many prostaglandins. In plants VLCFAs are major constituents of triacylglycerols in many seed oils, are essential precursors for cuticular wax production, and are utilized in the synthesis of glycosylceramides, an important component of the plasma membrane.

Obtaining detailed information on the biochemistry of KAS enzymes has been hampered by the difficulties encountered when purifying membrane bound enzymes. Although elongase activities have been partially purified from a number of sources, or studied using cell fractions, the elucidation of the biochemistry of elongase complexes has been hampered by the complexity of the membrane fractions used as the enzyme source. For example, until recently, it was unclear as to whether plant elongase complexes were composed of a multifunctional polypeptide similar to the FAS found in animals and yeast, or if the complexes existed as discrete and dissociable enzymes similar to the FAS of plants and bacteria. Partial purification of an elongase KAS, immunoblot identification of the hydroxy acyl dehydrase, and the recent cloning of a KAS gene (FAEL) suggest that the enzyme activities of elongase complexes exist on individual enzymes.

SUMMARY OF THE INVENTION

The invention disclosed herein relates to an isolated polynucleotide selected from one of the following: SEQ ID NO:1; SEQ ID NO:3; SEQ ID NO:5; SEQ ID NO:7; SEQ ID NO:9; SEQ ID NO:11; SEQ ID NO:13; an RNA analog of SEQ ID NO:1, 3, 5, 7, 9, 11, 13, or 15; and a polynucleotide having a nucleic acid sequence complementary to one of the above. The polynucleotide can also be a nucleic acid fragment of one of the above sequences that is at least 15 nucleotides in length and that hybridizes under stringent conditions to genomic DNA encoding the polypeptide of SEQ ID NO:2, SEQ ID NO:4, SEQ ID NO:6, SEQ ID NO:8, SEQ ID NO:10, SEQ ID NO:12, or SEQ ID NO:14.

Also disclosed herein is an isolated polypeptide that has an amino acid sequence substantially identical to one of the following: SEQ ID NO:2, SEQ ID NO:4, SEQ ID NO:6, SEQ ID NO:8, SEQ ID NO:10, SEQ ID NO:12, or SEQ ID NO:14. Also disclosed are isolated polynucleotides encoding polypeptides substantially identical in their amino acid sequence to: SEQ ID NO:2, SEQ ID NO:4, SEQ ID NO:6, SEQ ID NO:8, SEQ ID NO:10, SEQ ID NO:12, or SEQ ID NO:14.

The invention also relates to a transgenic plant containing a nucleic acid construct. The nucleic acid construct comprises a polynucleotide described above. The construct further comprises a regulatory element operably linked to the polynucleotide. The regulatory element may a tissue-specific promoter, for example, an epidermal cell-specific promoter or a seed-specific promoter. The regulatory element may be operably linked to the polynucleotide in sense or antisense orientation. The plant has altered levels of very long chain fatty acids in tissues where the polynucleotide is expressed, compared to a parental plant lacking the nucleic acid construct.

A method is disclosed for altering the levels of very long chain fatty acids in a plant. The method comprises the steps of creating a nucleic acid construct and introducing the construct into the plant. The construct includes a polynucleotide selected from one of the following: SEQ ID NO:1; SEQ ID NO:3; SEQ ID NO:5; SEQ ID NO:7; SEQ ID NO:9; SEQ ID NO:11; SEQ ID NO:13; an RNA analog of SEQ ID NO:1, 3, 5, 7, 9, 11, 13, or 15; and a polynucleotide having a nucleic acid sequence complementary to one of the above. The polynucleotide can also be a nucleic acid fragment of one of the above that is at least 15 nucleotides in length and that hybridizes under stringent conditions to genomic DNA encoding the polypeptide of SEQ ID NO:2, SEQ ID NO:4, SEQ ID NO:6, SEQ ID NO:8, SEQ ID NO:10, SEQ ID NO:12, or SEQ ID NO:14. The polynucleotide is effective for altering the levels of very long chain fatty acids in the plant.

Other features and advantages of the invention will be apparent from the following description of the preferred embodiments thereof, and from the claims.

BRIEF DESCRIPTION OF THE DRAWINGS

FIG. 3 shows the nucleotide sequence of the coding region of the Arabidopsis EL1 polynucleotide (SEQ ID NO:1).

FIG. 4 shows the deduced amino acid sequence (SEQ ID NO:2) for the EL1 coding sequence of FIG. 3.

FIG. 5 shows the nucleotide sequence of the coding region of the Arabidopsis EL2 polynucleotide (SEQ ID NO:3).

FIG. 6 shows the deduced amino acid sequence (SEQ ID NO:4) for the EL2 coding sequence of FIG. 5.

FIG. 7 shows the nucleotide sequence of the coding region of the Arabidopsis EL3 polynucleotide (SEQ ID NO:5).

FIG. 8 shows the deduced amino acid sequence (SEQ ID NO:6) for the EL3 coding sequence of FIG. 7.

FIG. 9 shows the nucleotide sequence of the coding region of the Arabidopsis EL4 polynucleotide (SEQ ID NO:7).

FIG. 10 shows the deduced amino acid sequence (SEQ ID NO:8) for the EL4 coding sequence of FIG. 9.

FIG. 11 shows the nucleotide sequence of the coding region of the Arabidopsis EL5 polynucleotide (SEQ ID NO:9).

FIG. 12 shows the deduced amino acid sequence (SEQ ID NO:10) for the EL5 coding sequence of FIG. 11.

FIG. 13 shows the nucleotide sequence of the coding region of the Arabidopsis EL6 polynucleotide (SEQ ID NO:11).

FIG. 14 shows the deduced amino acid sequence (SEQ ID NO:12) for the EL6 coding sequence of FIG. 13.

FIG. 15 shows the nucleotide sequence of the coding region of the Arabidopsis EL7 polynucleotide (SEQ ID NO:13).

FIG. 16 shows the deduced amino acid sequence (SEQ ID NO:14) for the EL7 coding sequence of FIG. 15.

DESCRIPTION OF THE PREFERRED EMBODIMENTS

Figure 1:
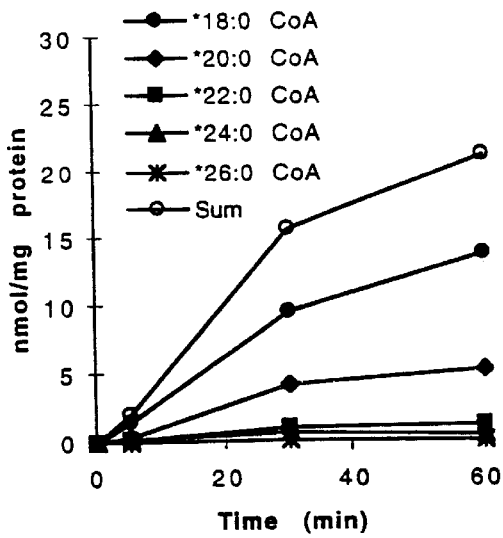
FIG. 1 shows the time course of in vitro VLCFA synthesis by FAE1 expressed in yeast, with 3 different acyl-CoA substrates.
Figure 1:
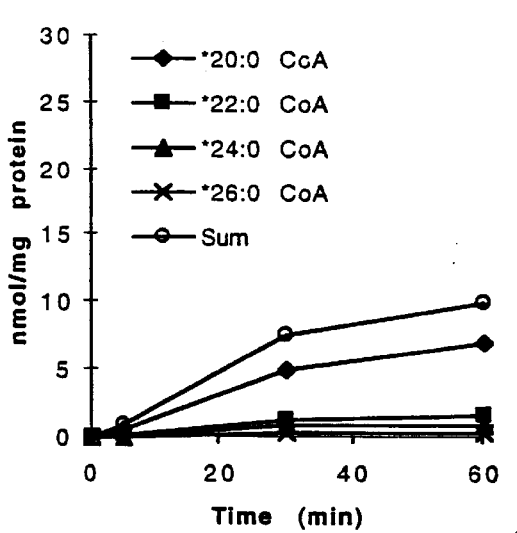
Figure 1:
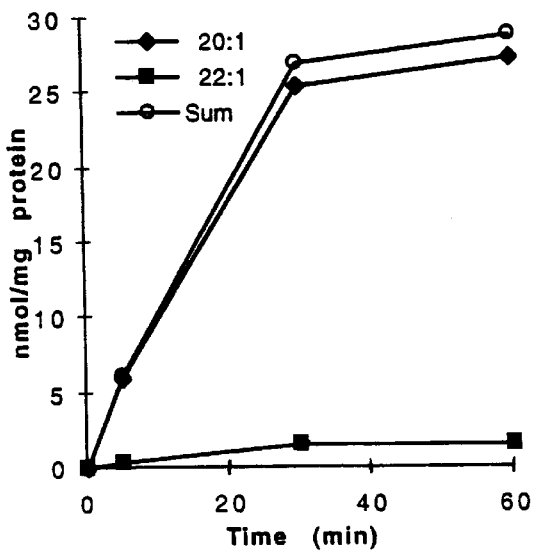

The present invention comprises isolated nucleic acids (polynucleotides) that encode polypeptides having β-ketoacyl synthase activity. The novel polynucleotides and polypeptides of the invention are involved in the synthesis of very long chain fatty acids and are useful for modulating the total amounts of such fatty acids and the specific VLCFA profile in plants.

A polynucleotide of the invention may be in the form of RNA or in the form of DNA, including cDNA, synthetic DNA or genomic DNA. The DNA may be double-stranded or single-stranded, and if single-stranded, can be either the coding strand or non-coding strand. An RNA analog may be, for example, mRNA or a combination of ribo- and deoxyribonucleotides. Illustrative examples of a polynucleotide of the invention are shown in FIGS. 3, 5, 7, 9, 11, 13 and 15.

A polynucleotide of the invention typically is at least 15 nucleotides (or base pairs, bp) in length. In some embodiments, a polynucleotide is about 20 to 100 nucleotides in length, or about 100 to 500 nucleotides in length. In other embodiments, a polynucleotide is greater than about 1500 nucleotides in length and encodes a polypeptide having the amino acid sequence shown in FIGS. 4, 6, 8, 10, 12, 14 or 16.

In some embodiments, a polynucleotide of the invention encodes analogs or derivatives of a polypeptide having the deduced amino acid sequence of FIGS. 4, 6, 8, 10, 12, 14 or 16. Such fragments, analogs or derivatives include, for example, naturally occurring allelic variants, non-naturally occurring allelic variants, deletion variants and insertion variants, that do not substantially alter the function of the polypeptide.

A polynucleotide of the invention may further comprise additional nucleic acids. For example, a nucleic acid fragment encoding a secretory or leading amino acid sequence can be fused in-frame to the amino terminal end of one of the EL1 through EL7 polypeptides. Other nucleic acid fragments are known in the art that encode amino acid sequences useful for fusing in-frame to the KAS polypeptides disclosed herein. See, e.g., U.S. Pat. No. 5,629,193 incorporated herein by reference. A polynucleotide may further comprise one or more regulatory elements operably linked to a KAS polynucleotide disclosed herein.

The present invention also comprises polynucleotides that hybridize to a KAS polynucleotide disclosed herein. Such a polynucleotide typically is at least 15 nucleotides in length. Hybridization typically involves Southern analysis (Southern blotting), a method by which the presence of DNA sequences in a target nucleic acid mixture are identified by hybridization to a labeled oligonucleotide or DNA fragment probe. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., (1989) *Molecular Cloning*, second edition, Cold Spring Harbor Laboratory, Plainview; N.Y.

A polynucleotide can hybridize under moderate stringency conditions or, preferably, under high stringency conditions to a KAS polynucleotide disclosed herein. High stringency conditions are used to identify nucleic acids that have a high degree of homology to the probe. High stringency conditions can include the use of low ionic strength and high temperature for washing, for example, 0.015 M NaCl/0.0015 M sodium citrate (0.1×SSC); 0.1% sodium lauryl sulfate (SDS) at 65° C. Alternatively, a denaturing agent such as formamide can be employed during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 pg/ml), 0.1% SDS, and 10% dextran sulfate at 42° C., with washes at 42° C. in 0.2×SSC and 0.1% SDS.

Moderate stringency conditions refers to hybridization conditions used to identify nucleic acids that have a lower degree of identity to the probe than do nucleic acids identified under high stringency conditions. Moderate stringency conditions can include the use of higher ionic strength and/or lower temperatures for washing of the hybridization membrane, compared to the ionic strength and temperatures used for high stringency hybridization. For example, a wash solution comprising 0.060 M NaCl/0.0060 M sodium citrate (4×SSC) and 0.1% sodium lauryl sulfate (SDS) can be used at 50° C., with a last wash in 1×SSC, at 65° C. Alternatively, a hybridization wash in 1×SSC at 37° C. can be used.

Hybridization can also be done by Northern analysis (Northern blotting), a method used to identify RNAs that hybridize to a known probe such as an oligonucleotide, DNA fragment, CDNA or fragment thereof, or RNA fragment. The probe is labeled with a radioisotope such as $^{32}$P, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

A polynucleotide has at least about 70% sequence identity, preferably at least about 80% sequence identity, more preferably at least about 90% sequence identity to SEQ ID NO:1, 3, 5, 7, 9, 11, or 13. Sequence identity can be determined, for example, by computer programs designed to perform single and multiple sequence alignments.

A polynucleotide of the invention can be obtained by chemical synthesis, isolation and cloning from plant genomic DNA or other means known to the art, including the use of PCR technology carried out using oligonucleotides corresponding to portions of SEQ ID NO:1, 3, 5, 7–9, 11 or 13. Polymerase chain reaction (PCR) refers to a procedure or technique in which target nucleic acid is amplified in a manner similar to that described in U.S. Pat. No. 4,683,195, incorporated herein by reference, and subsequent modifications of the procedure described therein. Generally, sequence information from the ends of the region of interest or beyond is employed to design oligonucleotide primers that are identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. Alternately, a cDNA library (in an expression vector) can be screened with KAS-specific antibody prepared using peptide sequence(s) from hydrophilic regions of the KAS protein of SEQ ID NO:2 and technology known in the art.

A polypeptide of the invention comprises an isolated polypeptide having the deduced amino acid sequence of FIGS. 2, 4, 6, 8, 10 and 12, as well as derivatives and analogs thereof. By "isolated" is meant a polypeptide that is expressed and produced in an environment other than the environment in which the polypeptide is naturally expressed and produced. For example, a plant polypeptide is isolated when expressed and produced in bacteria or fungi. Similarly, a plant polypeptide is isolated when its gene coding sequence is operably linked to a chimeric regulatory element and expressed in a tissue where the polypeptide is not naturally expressed. A polypeptide of the invention also comprises variants of the KAS polypeptides disclosed herein, as discussed above.

A full-length KAS coding sequence may comprise the sequence shown in SEQ ID NO:1, 3, 5, 7, 9, 11 or 13. Alternatively, a chimeric full-length KAS coding sequence may be formed by linking, in-frame, nucleotides from the 5' region of a first KAS gene to nucleotides from the 3' region a of a second KAS gene, thereby forming a chimeric KAS protein.

It should be appreciated that nucleic acid fragments having a nucleotide sequence other than the KAS sequences disclosed in SEQ ID NO:1, 3, 5, 7, 9, 11 or 13 will encode a polypeptide having the exemplified amino acid coding sequence of SEQ ID NO:2, 4, 6, 8, 10, 12 or 14, respectively. The degeneracy of the genetic code is well-known to the art; i.e., for many amino acids, there is more than one nucleotide triplet which serves as the codon for the amino acid.

It should also be appreciated that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Vol. 5, Suppl. 3, pp. 345–352, which is incorporated by reference herein, provides frequency tables for amino acid substitutions which can be employed as a measure of amino acid similarity.

A nucleic acid construct of the invention comprises a polynucleotide as disclosed herein linked to another, different polynucleotide. For example, a full-length KAS coding sequence may be operably fused in-frame to a nucleic acid fragment that encodes a leader sequence, secretory sequence or other additional amino acid sequences that may be usefully linked to a polypeptide or peptide fragment.

A transgenic plant of the invention contains a nucleic acid construct as described herein. In some embodiments, a transgenic plant contains a nucleic acid construct that comprises a polynucleotide of the invention operably linked to at least one suitable regulatory sequence in sense orientation. Regulatory sequences typically do not themselves code for a gene product. Instead, regulatory sequences affect the expression level of the polynucleotide to which they are linked. Examples of regulatory sequences are known in the art and include, without limitation, minimal promoters and promoters of genes preferentially or exclusively expressed in seeds or in epidermal cells of stems and leaves. Native regulatory sequences of the polynucleotides disclosed herein can be readily isolated by those skilled in the art and used in constructs of the invention. Other examples of suitable regulatory sequences include enhancers or enhancer-like elements, introns, 3' non-coding regions such as poly A sequences and other regulatory sequences discussed herein. Molecular biology techniques for preparing such chimeric genes are known in the art.

In other embodiments, a transgenic plant contains a nucleic acid construct comprising a partial or a full-length KAS coding sequence operably linked to at least one suitable regulatory sequence in antisense orientation. The chimeric gene can be introduced into a plant and transgenic progeny displaying expression of the antisense construct are identified.

One may use a polynucleotide disclosed herein for cosuppression as well as for antisense inhibition. Cosuppression of genes in plants may be achieved by expressing, in the sense orientation, the entire or partial coding sequence of a gene. See, e.g., WO 94/11516, incorporated herein by reference.

Transgenic techniques for use in the invention include, without limitation, Agrobacterium-mediated transformation, viral vector-mediated transformation electroporation and particle gun transformation. Illustrative examples of transformation techniques are described in U.S. Pat. No. 5,204,253, (particle gun) and U.S. Pat. No. 5,188,958 (Agrobacterium), incorporated herein by reference. Transformation methods utilizing the Ti and Ri plasmids of Agrobacterium spp. typically use binary-type vectors. Walkerpeach, C. et al., in Plant Molecular Biology Manual, S. Gelvin and R. Schilperoort, eds., Kluwer Dordrecht, C1:1–19 (1994). If cell or tissue cultures are used as the recipient tissue for transformation, plants can be regenerated from transformed cultures by techniques known to those skilled in the art.

Techniques are known for the introduction of DNA into monocots as well as dicots, as are the techniques for culturing such plant tissues and regenerating those tissues. Monocots which have been successfully transformed and regenerated include wheat, corn, rye, rice, and asparagus. See, e.g., U.S. Pat. Nos. 5,484,956 and 5,550,318, incorporated herein by reference.

For efficient production of transgenic plants from plant cells, it is desirable that the plant tissue used for transformation possess a high capacity for regeneration. Transgenic plants of woody species such as poplar and aspen have also been obtained. Technology is also available for the manipulation, transformation, and regeneration of gymnosperm plants. For example, U.S. Pat. No. 5,122,466 describes the biolistic transformation of conifers, with preferred target tissue being meristematic and cotyledon and hypocotyl tissues. U.S. Pat. No. 5,041,382 describes enrichment of conifer embryonal cells.

Seeds produced by a transgenic plant(s) can be grown and then selfed (or outcrossed and selfed) to obtain seeds homozygous for the construct. Seeds can be analyzed in order to identify those homozygotes having the desired expression of the construct. Transgenic plants may be entered into a breeding program, e.g., to introgress the novel construct into other lines, to transfer the construct to other species, or for further selection of other desirable traits. Alternatively, transgenic plants may be propagated vegetatively for those species amenable to such techniques. A nucleic acid construct of the invention can alter the levels of very long chain fatty acids in plant tissues expressing the polynucleotide, compared to VLCFA levels in corresponding tissues from an otherwise identical plant not expressing the polynucleotide. A comparison can be made, for example, between a non-transgenic plant of a plant line and a transgenic plant of the same plant line. Levels of VLCFAs having 20–32 carbons and/or levels of VLCFAs having 32–60 carbons can be altered in plants disclosed herein. Plants having an altered VLCFA composition may be identified by techniques known to the skilled artisan, e.g., thin layer chromatography or gas-liquid chromatography (GLC) analysis of the appropriate plant tissue.

A suitable group of plants with which to practice the invention are the Brassica species, including *B. napus, B. rapa, B.juncea*, and *B. hirta*. Other suitable plants include, without limitation, soybean (*Glycine max*), sunflower (*Helianthus annuus*) and corn (*Zea mays*).

A method according to the invention comprises introducing a nucleic acid construct into a plant cell and producing a plant (as well as progeny of such a plant) from the transformed cell. Progeny includes descendants of a particular plant or plant line, e.g., seeds developed on an instant plant are descendants. Progeny of an instant plant include seeds formed on $F_1$, $F_2$, $F_3$, and subsequent generation plants, or seeds formed on $BC_1$, $BC_2$, $BC_3$, and subsequent generation plants.

Methods and compositions according to the invention are useful in that the resulting plants and plant lines have desirable alterations in very long chain fatty acid composition. Suitable tissues in which to express polynucleotides and/or polypeptides of the invention include, without limitation, seeds, stems and leaves. Leaf tissues of interest include cells and tissues of the epidermis, e.g., cells that are involved in forming trichomes. Of particular interest are epidermal cells involved in forming the cuticular layer. The cuticular layer comprises various very long chain fatty acids and VLCFA derivatives such as alkanes, esters, alcohols and aldehydes. Altering the composition and amount of VLCFAs in epidermal cells and tissues may enhance defense mechanisms and drought tolerance of plants disclosed herein.

Polynucleotides of the invention can be used as markers in plant genetic mapping and plant breeding programs. Such markers may include RFLP, RAPD, or PCR markers, for example. Marker-assisted breeding techniques may be used to identify and follow a desired fatty acid composition during the breeding process. Marker-assisted breeding techniques may be used in addition to, or as an alternative to, other sorts of identification techniques. An example of marker-assisted breeding is the use of PCR primers that specifically amplify a sequence from a desired KAS that has been introduced into a plant line and is being crossed into other plant lines.

Plants and plant lines disclosed herein preferably have superior agronomic properties. Superior agronomic characteristics include, for example, increased seed germination percentage, increased seedling vigor, increased resistance to seedling fungal diseases (damping off, root rot and the like), increased yield, and improved standability.

While the invention is susceptible to various modifications and alternative forms, certain specific embodiments thereof are described in the general methods and examples set forth below. It should be understood, however, that these examples are not intended to limit the invention to the particular forms disclosed but, instead the invention is to cover all modifications, equivalents and alternatives falling within the scope of the invention.

EXAMPLES

Example 1

Cloning and Expression of FAE1 in Yeast Cells

The open reading frame of the Arabidopsis FAE1 gene was amplified directly by PCR, using *Arabidopsis thaliana* cv. Columbia genomic DNA as a template, pfu DNA polymerase and the following primers: 5' CTCGAGGAGCAATGACGTCCGTTAA-3' and 5'-CTCGAGTTAGGACCGACCGTTTTG-3' (SEQ ID NO:15 and 16, respectively. The PCR product was blunt-end cloned into the Eco RV site of pBluescript (Stratagene, La Jolla, Calif.), The FAE1 gene was excised from the Bluescript vector with BamH1, and then subcloned into the pYEUra3 (Clontech, Palo Alto, Calif.). pYEUra3 is a yeast centromere-containing, episomal plasmid that is propagated stably through cell division. The FAE1 gene was inserted downstream of a GAL1 promoter in pYEUra3. The GAL1 promoter is induced when galactose is present in the medium and repressed when glucose is present in the growth medium.

Insertion of the FAE1 gene in the sense orientation was confirmed by PCR, and pYEUra3/FAE1 was used to transform *Saccharomyces cerevisiae* strain AB1380 using a lithium acetate procedure as described in Gietz, R. and Woods, R., in Molecular Genetics of Yeast: Practical Approaches, Oxford Press, pp. 121–134 (1994). Plasmid DNA was isolated from putative transformants, and the presence of the FAE1/pYEUra3 construct was confirmed by Southern analysis.

Yeast transformed with pYEUra3 having FAE1 operably linked to the GAL1 promoter were grown in the presence of galactose or glucose and were analyzed for the expression of FAE1. As a control, yeast transformed with pYEUra3 containing no insert were also assayed. Analysis of such control preparations yielded fatty acid compositions and fatty acid elongation rates similar to those of yeast transformed with pYEUra3/FAE1 and grown with glucose as the carbon source.

The fatty acid composition of yeast cells grown in the presence of galactose was compared to that of cells grown in the presence of glucose, to determine if VLCFA were found in the galactose-induced cells.

Transformed yeast cells were grown overnight in YPD media at 30° C. with vigorous shaking. One hundred $\mu$l of the overnight culture were used to inoculate 40 ml of complete minimal uracil dropout media (CM-Ura) supplemented with either glucose or galactose (2% w/v). Cultures were grown at 30° C. to an $OD_{600}$ of approximately 1.3 to 1.5. Cells were harvested by centrifugation at 5000×g for 10 min. Total lipids were extracted from the cells with 2 volumes of 4N KOH in 100% methanol for 60 min. at 80° C. Fatty acids were saponified and methyl esters were prepared by drying the samples and resuspending in 0.5 ml of boron trichloride in methanol (10% v/v). Samples were incubated at 50° C. for 15 min in a sealed tube. About 2 ml of water was then added and the fatty methyl esters were extracted thrice with 1 ml of hexane. Extracts were dried under nitrogen and redissolved in hexane. See Hlousek-Radojcic, A. et al., Plant J. 8:803–809. Methyl esters were analyzed on an HP 5890 series II gas chromatograph equipped with a 5771MSD and 7673 auto injector (Hewlett-Packard, Cincinnati, Ohio). Methyl esters were separated on a DB-23 (J&W Scientific) capillary column (30 m×0.25 mm×0.25 $\mu$m). The column was operated with helium carrier gas and splitless injection (injection temperature 280° C., detector temperature 280° C.). After an initial 3 min. at 100° C., the oven temperature was raised to 250° at 20° C. $min^{-1}$ and maintained at that temperature for an additional 3 min. The identity of the peaks was verified by cochromatography with authentic standards and by mass spectrometer analysis.

The results clearly revealed the appearance of both 20:1 and 22:1 acyl-CoA products in galactose-induced yeast containing the FAE1 coding sequence. Uninduced yeast cells failed to accumulated significant amounts of fatty acids longer than C18. These results indicate that expression of FAE1 in yeast resulted in functional KAS activity and functional elongase activity.

Example 2

FAE1 Activity in Yeast Microsomes

The functional expression of the FAE1 KAS was analyzed by isolating microsomes from transformed yeast cells and assaying these microsomes in vitro for elongase activity.

Transformed yeast cells were grown in the presence of either glucose or galactose (2% w/v) as described in Example 1. Cells were harvested by centrifugation at 5000×g for 10 min and washed with 10 ml ice cold isolation buffer (IB), which contains 80 mM Hepes-KOH, pH 7.2, 5 mM EGTA, 5 mM EDTA, 10 mM KCl, 320 mM sucrose and 2 mM DTT). Cells were then resuspended in enough IB to fill a 1.7 ml tube containing 700 $\mu$l of 0.5 $\mu$m glass beads and yeast microsomes were isolated from the cells essentially as described in Tillman, T. and Bell, R., J. Biol. Chem. 261:9144–9149 (1986). The microsomal membrane pellet was recovered by centrifugation at 252,000×g for 60 min. The pellet was rinsed by resuspending in 40 ml fresh IB and again recovered by centrifugation at 252000×g for 60 min. Microsomal pellets were resuspended in a minimal volume of IB, and the protein concentration adjusted to 2.5 $\mu$g $\mu l^{-1}$ by addition of IB containing 15% glycerol. Microsomes were frozen on dry ice and stored at −80° C. The protein concentration in microsomes was determined by the Bradford method (Bradford, 1976).

Fatty acid elongase activity was measured essentially as described in Hlousek-Radojcic, A. et al., Plant J. 8:803–809 (1995). Briefly, the standard elongation reaction mix contained 80 mM Hepes-KOH, pH 7.2, 20 mM $MgCl_2$, 500 $\mu$M NADPH, 1 mM ATP, 100 uM malonyl-CoA, 10 $\mu$M COA-SH and 15 $\mu$M radioactive acyl-CoA substrate. The radiolabeled substrate was either $[1-^{14}C]18:1$-CoA (50 uCi $\mu mol^{-1}$), $[1-^{14}C]$ 18:0-CoA (55 uCi $\mu mol^{-1}$), or $[1-^{14}C]$ 16:0-COA (54 uCi $\mu mol^{-1}$). The reaction was initiated by the addition of yeast microsomes (5 $\mu$g protein) and the mixture incubated at 30° C. for the indicated period of time. The final reaction volume was 25 $\mu$l.

Methyl esters of the acyl-CoA elongation products were prepared as described in Example 1. Methyl esters were separated on reversed phase silica gel KC18 TLC plates (Whatman, 250 uM thick), quantified by phosphorimaging, and analyzed on by ImageQuant software (Molecular Dynamics, Inc., Sunnyvale, Calif.). The detection limit for each product is about 0.001 nanomoles per min. per mg microsomal protein, depending on the phosphorimage exposure time.

Figure 2:
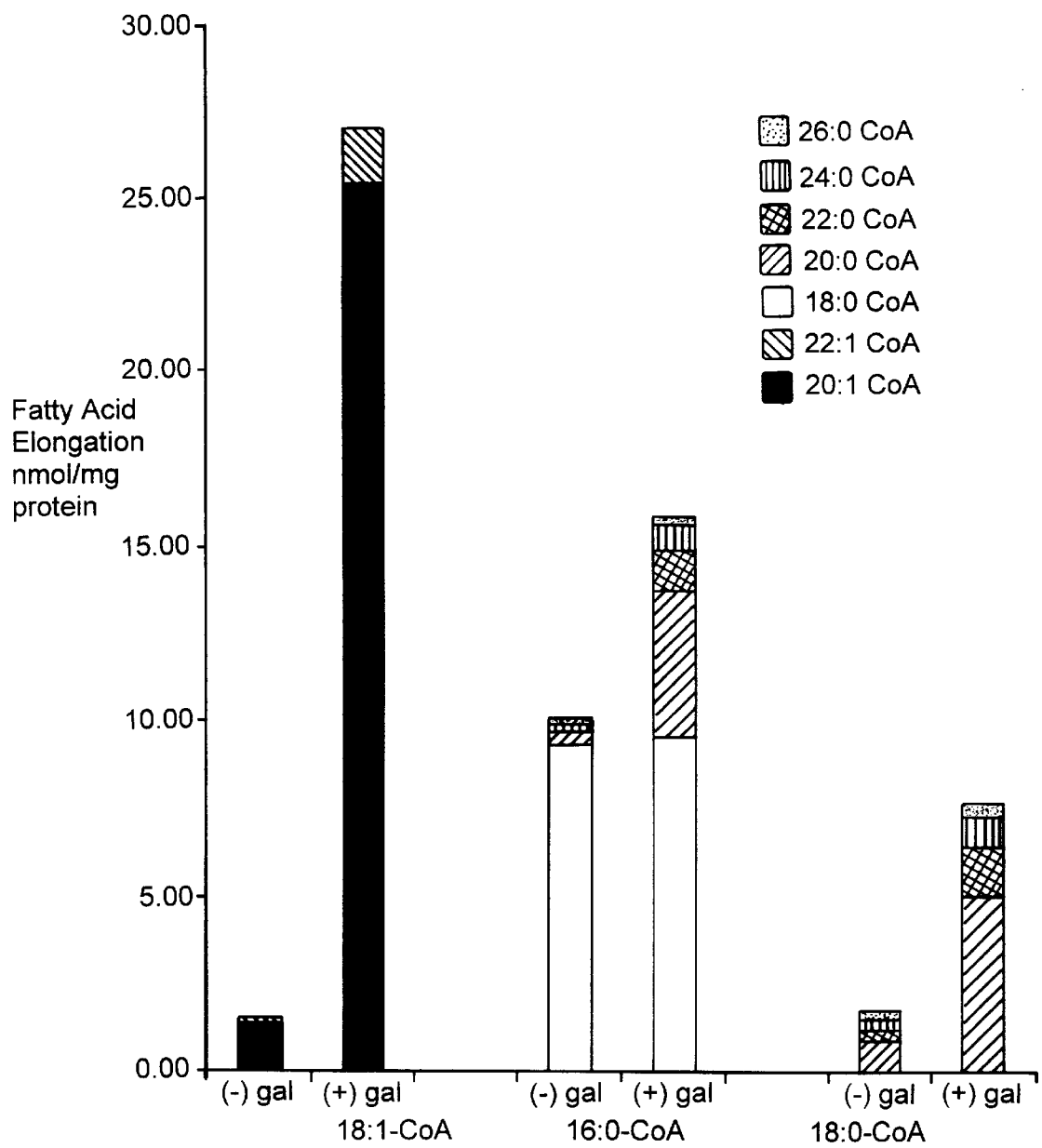
FIG. 2 shows the rates of in vitro VLCFA synthesis and the VLCFA profiles of FAE1 expressed in yeast, with 3 different acyl-CoA substrates.

Results of representative in vitro elongation assays are shown in FIGS. 1 and 2. The results indicate that microsomes from galactose-induced cells expressing FAE1 catalyzed multiple cycles of elongation starting with either C16:0 acyl CoA, C18:0 acyl CoA, or C18:1 acyl-CoA as the substrate (FIG. 1). The 16:0 and 18:0 acyl-CoA substrates were elongated to C26:0 acyl-CoA. In contrast, the 18:1-CoA substrate was elongated primarily to C20:1, with only low levels of C22:1 acyl-CoA being produced. occasionally, trace levels of C24:1 CoA were also observed. Although the chain length of the products from the 18:1 acyl-CoA substrate were less than the chain length from the saturated acyl-CoA substrates, the rate of elongation of oleoyl-CoA was about 2- and 3-fold higher than the rates of elongation of 16:0-CoA and 18:0-CoA, respectively.

The elongation activity observed in microsomes from uninduced cells indicated that there was a low level of endogenous elongase activity when 18:1-CoA or 18:0-CoA were used as substrates. There was substantial 16:0-CoA elongase activity (10.1 nmol mg protein$^{-1}$ at 30 min) in microsomes from uninduced cells (FIG. 2). However, the major product of 16:0 elongation using uninduced microsomes was C18:0 acyl CoA, with only small amounts of products beyond this length. The elongation of the 16:0 acyl-CoA substrate presumably is due to an endogenous yeast elongase.

Elongation of 18:1 CoA by microsomes from induced cells occurred at a rate about 18-fold higher than in microsomes isolated from the uninduced cells (FIG. 2). With microsomes from induced yeast, synthesis of 20:0 CoA from the 16:0 CoA substrate, occurred at a rate similar to that seen when the substrate was 18:0 CoA (4.2 vs. 5.1 nmol mg protein$^{-1}$). The total rate of elongation of [$^{14}$C] 16:0-CoA by microsomes from induced cells (15.8 nmol mg protein$^{-1}$ at 30 min.) was more than 50% higher than elongation of [$^{14}$C] 16:0-CoA by microsomes from uninduced cells, suggesting that the FAE1 KAS utilized 16:0-CoA as a substrate in addition to C18–C24 acyl-CoAs. The FAE1 elongase KAS activity, i.e., the difference in the 16:0 elongation rates between microsomes from induced and uninduced cells, was 5.7 nmol mg protein$^{-1}$. The elongation rate with the 16:0 substrate thus was similar to the elongase activity of the FAE1 elongase KAS with the 18:0 substrate.

These results indicate that FAE1 KAS expressed in yeast could synthesize 3-ketoacyl-CoA in vitro and, in combination with yeast reductases and dehydrases, could form a functional VLCFA elongase complex. In addition, these results suggest that FAE1 is membrane-bound in yeast cells.

Example 3

Cloning and Sequencing of Arabidopsis Elongase Genes

The sequence of a jojoba seed cDNA (see WO 93/10241 and WO 95/15387, incorporated herein by reference) was used to search the Arabidopsis expressed sequence tag (EST) database of the Arabidopsis Genome Stock Center (The Ohio State University, Columbus, Ohio). The BLAST computer program (National Institutes of Health, Bethesda, Md., USA) was used to perform the search. The search identified two ESTs (ATTS1282 and ATTS3218) that had a high degree of sequence identity with the jojoba sequence. The ATTS1282 and ATTS3218 ESTs appeared to be partial cDNA clones rather than full-length clones based on the length of the jojoba sequence.

A genomic DNA library from Arabidopsis thaliana cv. Columbia, was prepared in the lambda GEM11 vector (Promega, Madison, Wis.) and was obtained from Ron Davis, Stanford University, Stanford, Calif. The library was hybridized with ATTS1282 and ATTS3218 as probes and 2 clones were identified for each EST. Phage DNA was isolated from each of the hybridizing clones, the genomic insert was excised with the restriction enzyme Sac I and subcloned into the plasmid pBluescript (Stratagene, La Jolla, Calif.). One clone from the ATTS1282 hybridization was designated EL1 and one clone from the ATTS3218 hybridization was designated EL2.

A yeast expression library, containing cDNA from *Arabidopsis thaliana* cv. Columbia, was prepared in the lambda YES expression vector described in Elledge et al. (Elledge, S. et al., Proc. Natl. Acad. Sci USA 88:1731–1735 (1991) and was obtained from Ron Davis at Stanford University, Stanford, Calif. The library was hybridized with a EL2 partial cDNA probe. A full-length EL2 cDNA was not identified. However, the probe did identify a full-length cDNA which was designated EL3.

A consensus sequence for the C-terminal region of EL1, EL2 and the jojoba cDNA polypeptides was identified by sequence alignment using DNA analysis programs from DNAStar, Madison, Wis. This consensus sequence was used to search the Arabidopsis EST database again for β-keto acyl synthase sequences. These searches identified four additional putative β-keto acyl synthase ESTs, which were designated EL4 through EL7. EL4, EL5, EL6, and EL7 have homology to Genbank Accession Nos. T04345, T44939, T22193 and T76700, respectively.

The lambda YES cDNA expression library described above was hybridized with the EL1 and EL4–EL7 ESTs as probes. This screen identified full-length cDNAs for EL1, EL5 and EL6.

The lambda GEM11 genomic library was hybridized with the EL4 and EL7 ESTs as probes. This screen identified full-length genomic clones for EL4 and EL7. Phage DNA was isolated from each of the hybridizing clones and subcloned into pBluescript as described above.

The 7 EL clones were sequenced on both strands with regions of overlap for each sequence run. Sequencing was carried out with an ABI automated sequencer (Applied Biosystems, Inc., Foster City, Calif.), following the manufacturer's instructions.

The nucleotide sequences for the coding regions of EL1–EL7 are shown in FIGS. 3, 5, 7, 9, 11, 13 and 15, respectively. The deduced amino acid sequences for EL1–EL7 are shown in FIGS. 4, 6, 8, 10, 12, 14 and 16, respectively, using the standard one-letter amino acid code. The EL1, EL2 and EL7 genomic clones appeared to lack introns. The EL4 genomic clone contained one intron near the 5' end of the coding region.

The nucleotide sequences of the 7 EL polynucleotides were compared to 5 DNA sequences present in Genbank. Genbank, National Center for Biotechnology Information, Bethesda, Md. Two of the 5 accessions were cloned from members of the Brassicaceae: the Arabidopsis FAE1 sequence (Accession U29142) and a *Brassica napus* sequence (Accession U50771). Three of the accessions were cloned from jojoba (*Simmondsia chinensis*): 2 wax biosynthesis genes (Accessions I14084 and I14085) and a jojoba KAS gene (Accession U37088). See also U.S. Pat. No. 5,445,947, incorporated herein by reference.

Multiple alignment of the 12 sequences was carried out with a computer program sold under the trade name MEGA-LIGN Lasergene by DNAStar (Madison, Wis.). Alignments were done using the Clustal method with weighted residue weight table. The nucleotide sequence similarity index and percent divergence based on the multiple alignment algorithm is shown in Table 1. The nucleotide sequences of EL1–EL7 are distinguishable from the 5 DNA sequences obtained from Genbank.

The deduced amino acid sequences of the EL1–7 polypeptides were compared with the MEGALIGN program to the deduced amino acid sequences of the same 5 Genbank clones, using the Clustal method with PAM250 residue weight table. The amino acid sequence similarity and percent divergence are shown in Table 2. The amino acid sequences of EL1–EL7 polypeptides are distinguishable from those of the Genbank sequences.

In the first experiment, microsomes were prepared from galactose-induced cultures of EL1, EL2 and FAE1, and incubated with either [1–$^{14}$C] 18:0 acyl-CoA or [1–$^{14}$C]

TABLE 1

Nucleotide sequence pair distances of EL1–EL7, using Clustal method with weighted residue weight table.

|    | 1    | 2    | 3    | 4    | 5    | 6    | 7    | 8    | 9    | 10   | 11   | 12   |    |                 |
|----|------|------|------|------|------|------|------|------|------|------|------|------|----|-----------------|
| 1  |      | 77.5 | 62.4 | 58.8 | 57.0 | 54.9 | 47.0 | 42.8 | 42.9 | 43.1 | 44.7 | 41.3 | 1  | ARAFAE1 U29142  |
| 2  | 18.1 |      | 61.0 | 57.9 | 55.4 | 53.7 | 46.9 | 42.7 | 44.1 | 42.9 | 42.3 | 40.5 | 2  | BNaFAE1 U50771  |
| 3  | 40.4 | 41.0 |      | 70.5 | 59.3 | 56.4 | 46.7 | 48.5 | 48.1 | 48.6 | 46.5 | 43.5 | 3  | EL2             |
| 4  | 43.9 | 44.3 | 28.0 |      | 56.3 | 55.4 | 46.5 | 47.0 | 45.1 | 47.2 | 47.4 | 42.3 | 4  | EL3             |
| 5  | 40.7 | 42.3 | 45.0 | 45.0 |      | 68.0 | 54.0 | 46.8 | 46.6 | 46.4 | 49.0 | 47.2 | 5  | EL5             |
| 6  | 45.8 | 48.9 | 46.0 | 47.3 | 32.4 |      | 53.6 | 48.6 | 48.2 | 48.6 | 49.0 | 49.2 | 6  | EL7             |
| 7  | 74.1 | 71.0 | 69.4 | 67.3 | 64.3 | 64.5 |      | 49.8 | 49.2 | 49.8 | 47.7 | 48.2 | 7  | EL6             |
| 8  | 68.1 | 66.2 | 63.4 | 63.1 | 65.5 | 64.2 | 56.1 |      | 97.7 | 99.7 | 48.4 | 45.8 | 8  | JOJOKCS U37088  |
| 9  | 67.0 | 65.4 | 63.7 | 64.6 | 64.6 | 64.1 | 56.6 | 1.1  |      | 95.9 | 47.6 | 44.8 | 9  | JOKCS10 I14084  |
| 10 | 67.2 | 65.2 | 61.8 | 61.4 | 64.1 | 63.0 | 56.3 | 0.2  | 1.1  |      | 48.4 | 45.3 | 10 | JOKCS11 I14085  |
| 11 | 88.6 | 85.8 | 81.0 | 77.0 | 77.4 | 82.4 | 83.1 | 71.1 | 71.1 | 69.9 |      | 48.3 | 11 | EL1             |
| 12 | 95.7 | 90.4 | 95.4 | 91.5 | 84.5 | 82.8 | 91.9 | 73.4 | 73.8 | 73.3 | 59.9 |      | 12 | EL4             |
|    | 1    | 2    | 3    | 4    | 5    | 6    | 7    | 8    | 9    | 10   | 11   | 12   |    |                 |

TABLE 2

Amino acid sequence pair distances of EL1–EL7, using Clustal method with PAM250 residue weight table.

|    | 1    | 2    | 3    | 4    | 5    | 6    | 7    | 8    | 9    | 10   | 11   | 12   |    |                 |
|----|------|------|------|------|------|------|------|------|------|------|------|------|----|-----------------|
| 1  |      | 72.0 | 62.9 | 59.8 | 60.9 | 60.2 | 50.3 | 51.9 | 52.1 | 51.5 | 49.1 | 42.0 | 1  | EL2             |
| 2  | 31.1 |      | 60.1 | 57.5 | 58.7 | 57.1 | 49.8 | 49.8 | 50.0 | 49.2 | 49.6 | 44.4 | 2  | EL3             |
| 3  | 47.4 | 48.7 |      | 82.4 | 60.7 | 63.0 | 50.0 | 51.4 | 51.6 | 50.8 | 47.8 | 43.9 | 3  | ATFAE1 U29142   |
| 4  | 51.8 | 52.8 | 17.9 |      | 60.2 | 61.0 | 49.2 | 50.3 | 50.5 | 49.7 | 46.5 | 42.4 | 4  | BNFAE1 U50771   |
| 5  | 49.0 | 51.3 | 45.8 | 46.2 |      | 75.8 | 61.0 | 58.7 | 58.9 | 58.3 | 55.0 | 55.6 | 5  | EL7             |
| 6  | 52.6 | 55.5 | 42.8 | 46.5 | 29.3 |      | 61.8 | 55.7 | 55.7 | 54.9 | 52.9 | 50.5 | 6  | EL5             |
| 7  | 74.7 | 70.5 | 71.8 | 74.4 | 52.0 | 50.8 |      | 52.8 | 52.8 | 51.8 | 53.4 | 51.6 | 7  | EL6             |
| 8  | 66.7 | 69.2 | 66.2 | 67.3 | 54.8 | 59.8 | 67.7 |      | 99.8 | 96.9 | 53.1 | 52.0 | 8  | JOJKCS U37088   |
| 9  | 66.3 | 68.7 | 66.2 | 67.3 | 54.0 | 59.3 | 67.7 | 0.2  |      | 96.9 | 53.1 | 51.9 | 9  | JKCS11 I14085   |
| 10 | 66.3 | 69.7 | 66.6 | 67.8 | 54.5 | 60.7 | 68.6 | 1.8  | 1.6  |      | 51.7 | 50.7 | 10 | JKCS10 I14084   |
| 11 | 73.6 | 73.7 | 72.8 | 74.4 | 60.8 | 66.0 | 67.2 | 63.9 | 63.9 | 65.3 |      | 50.8 | 11 | EL1             |
| 12 | 84.6 | 85.5 | 82.7 | 83.3 | 60.6 | 70.8 | 67.1 | 68.5 | 68.5 | 69.9 | 69.4 |      | 12 | EL4             |
|    | 1    | 2    | 3    | 4    | 5    | 6    | 7    | 8    | 9    | 10   | 11   | 12   |    |                 |

Example 4

Expression of EL1 and EL2 in Yeast

The open reading frames (ORFs) for the EL2, EL4 and EL7 clones were amplified by PCR. The EL2 ORF was cloned into λYES using the primers: CTCGAGCAAGTC-CACTACCACGCA and CTCGAGCGAGTCAGAAG-GAACAAA (SEQ ID NO:17 and 18, respectively). The EL4 ORF was cloned into pYEUra3 using the primers: GATAATTTAGAGAGGCACAGGGT and GTCGACA-CAAGAATGGGTAGATCCAA (SEQ ID NO:19 and 20, respectively). The EL7 ORF was cloned into pYEUra3 using the primers: CAGTTCCTCAAACGAAGCTA and GTC-GACTTCTCAATGGACGGTGCCGGA (SEQ ID NO:19 NO:21 and 22, respectively). Amplified products were cloned into pYEUra3 under the control of, and 3' to, the GAL1 promoter. The resulting plasmids were transformed into yeast as described in Example 1.

Yeast cultures containing full-length EL1 in λYES and full-length EL2 in pYEUra3 were grown in the presence of galactose or glucose as described in Example 2. Microsomes were then prepared from each of the cultures and fatty acid elongation assays were carried out as described in Example 2.

18:1 acyl-CoA as substrate. The amounts of various reaction products synthesized after 30 minutes (min) were determined as described in Example 2. The results when 18:0 acyl-CoA was the substrate are shown in Table 3. The results when 18:1 acyl-CoA was the substrate are shown in Table 4.

TABLE 3

Elongation of 18:0-CoA by FAE1, EL1 and EL2 Genes Expressed in Yeast

| Acyl-CoA | β-Keto Acyl Synthase Gene | | | | | |
|---|---|---|---|---|---|---|
| | FAE1 | | EL1 | | EL2 | |
| Product | Rate[1] | (%) | Rate | (%) | Rate | (%) |
| 20:0 | 0.369 | 64.3 | 0.084 | 38.8 | 0.108 | 41.8 |
| 22:0 | 0.113 | 18.6 | 0.047 | 21.9 | 0.053 | 20.7 |
| 24:0 | 0.065 | 10.7 | 0.043 | 19.9 | 0.052 | 20.3 |
| 26:0 | 0.038 | 6.3 | 0.042 | 19.4 | 0.044 | 17.2 |
| Total | 0.585 | 100.0 | 0.216 | 100.0 | 0.258 | 100.0 |

[1]Nanomoles/minute/mg of microsomal protein

TABLE 4

Elongation of 18:1-CoA by FAE1, EL1 and EL2 Genes Expressed in Yeast

| Acyl-CoA Product | β-Keto Acyl Synthase Gene | | | | | |
|---|---|---|---|---|---|---|
| | FAE1 | | EL1 | | EL2 | |
| | Rate[1] | (%) | Rate | (%) | Rate | (%) |
| 20:1 | 1.131 | 84.6 | 0.111 | 80.8 | 0.091 | 84.1 |
| 22:1 | 0.206 | 15.4 | 0.026 | 19.2 | 0.017 | 15.9 |
| 24:1 | 0.0 | 0.0 | 0.0 | 0.0 | 0.0 | 0.0 |
| 26:1 | 0.0 | 0.0 | 0.0 | 0.0 | 0.0 | 0.0 |
| Total | 1.337 | 100.0 | 0.137 | 100.0 | 0.108 | 100.0 |

[1]Nanomoles/minute/mg of microsomal protein

The results shown in Tables 3 and 4 indicate that the EL1 and EL2 gene products have β-ketoacyl synthase (KAS) activity and that the KAS reaction product can be utilized to form VLCFAs. The specific activities of the 3 KAS enzymes cannot be compared, since the relative amount of the heterologous KAS protein in each microsomal preparation is not known. However, the proportions of various reaction products can be compared between FAE1, EL1 and EL2.

The data shown in Table 3 indicate that the EL1 and EL2 KAS activities result in a higher proportion of saturated VLCFAs than does the FAE1 KAS activity. These results suggest that EL1 and EL2 encode novel gene products, because EL1 and EL2 have a greater preference for C22:0 and C24:0 acyl-CoA substrates than does FAE1.

A comparison of the relative elongation activity of FAE1 with 18:0 and 18:1 substrates (Tables 3 and 4) indicates that FAE1 is more active when 18:1 is the substrate than when 18:0 is the substrate. In contrast, the overall rate of product formation with EL1 is less when 18:1 is the substrate than when 18:0 is the substrate (Tables 3 and 4). EL2 is also less active when 18:1 is the substrate than when 18:0 is the substrate (Tables 3 and 4). These results support the conclusion that EL1 and EL2 encode novel gene products and suggest that EL1 and EL2 have a preference for saturated fatty acids as substrates, whereas the FAE1 gene product has a preference for monounsaturated fatty acids as substrates.

In a second experiment, microsomes were prepared from galactose-induced and from glucose-repressed yeast cultures containing EL1 or EL2 coding sequences. The microsomal preparations were incubated with either 18:0 acyl-CoA or 18:1 acyl-CoA as substrate and the fatty acid reaction products determined as described above. The results with the 18:0 substrate are shown in Table 5. The results with the 18:1 substrate are shown in Table 6.

TABLE 5

Elongation of 18:0-CoA by EL1 and EL2 With and Without Induction of Gene Expression

| Acyl CoA | β-Keto Acyl Synthase Gene | | | | | | | |
|---|---|---|---|---|---|---|---|---|
| | EL1 | | | | EL2 | | | |
| | + Glucose | | + Galactose | | + Glucose | | + Galactose | |
| | Rate[1] | (%) | Rate | (%) | Rate | (%) | Rate | (%) |
| 20:0 | 0.007 | 100.0 | 0.074 | 55.8 | 0.030 | 81.3 | 0.107 | 43.1 |
| 22:0 | 0.000 | 0.0 | 0.023 | 17.4 | 0.002 | 5.1 | 0.044 | 17.8 |
| 24:0 | 0.000 | 0.0 | 0.020 | 15.3 | 0.005 | 13.6 | 0.048 | 19.1 |
| 26:0 | 0.000 | 0.0 | 0.015 | 11.5 | 0.000 | 0.0 | 0.050 | 20.0 |
| Total | 0.007 | 100.0 | 0.133 | 100.0 | 0.037 | 100.0 | 0.249 | 100.0 |

[1]Nanomoles/minute/mg of microsomal protein

TABLE 6

Elongation of 18:1-CoA by EL1 and EL2 With and Without Induction of Gene Expression

| Acyl COA | β-Keto Acyl Synthase Gene | | | | | | | |
|---|---|---|---|---|---|---|---|---|
| | EL1 | | | | EL2 | | | |
| | + Glucose | | + Galactose | | + Glucose | | + Galactose | |
| | Rate[1] | (%) | Rate | (%) | Rate | (%) | Rate | (%) |
| 20:1 | 0.062 | 100.0 | 0.081 | 100.0 | 0.043 | 100.0 | 0.089 | 100.0 |
| 22:1 | 0.000 | 0.0 | 0.000 | 0.0 | 0.000 | 0.0 | 0.000 | 0.0 |
| 24:1 | 0.000 | 0.0 | 0.000 | 0.0 | 0.000 | 0.0 | 0.000 | 0.0 |
| 26:1 | 0.000 | 0.0 | 0.000 | 0.0 | 0.000 | 0.0 | 0.000 | 0.0 |
| Total | 0.062 | 100.0 | 0.081 | 100.0 | 0.043 | 100.0 | 0.089 | 100.0 |

[1]Nanomoles/minute/mg of microsomal protein

The results in Table 5 show in vitro elongase activity for EL1 and EL2 under induced (galactose) and uninduced (glucose) conditions. The comparison indicates that induction with galactose results in a large increase in overall elongase activity when 18:0 acyl CoA is the substrate (about 19-fold and 7-fold for EL1 and EL2, respectively). In contrast, induction when 18:1 acyl CoA is the substrate results in only a small increase in elongase activity (about 1.3-fold and 2-fold for EL1 and E12, respectively), as shown in Table 6.

The results in Table 5 show that little or no VLCFA products are made by yeast microsomes under uninduced conditions. Upon induction of EL1 and EL2 gene expression, however, significant quantities of C20:0, C22:0, C24:0 and C26:0 are made. The data in Tables 5 and 6 are consistent with the results in Tables 3 and 4, which indicated that EL1and EL2 were more active with a saturated fatty acid substrate than with a monounsaturated substrate.

The data in Tables 5 and 6 are also consistent with the data in Tables 3 and 4 indicating that the EL1 and EL2 gene products are more active in converting C24:0 to C26:0 than is FAE1.

In a third experiment, microsomes from induced and uninduced cultures containing EL1 or EL2 were incubated in the absence of cofactors involved in the β-ketoacyl condensation reaction. Cultures were induced and microsomes were prepared as described in Example 2. In vitro assays were carried out as described in Example 2, except that either ATP, COASH or both were omitted from the enzyme reaction mixture. In addition, one reaction was carried out in a complete mixture having 0.01 mM of cerulenin (Sigma, St. Louis, Mo.). Cerulenin is an inhibitor of some condensing enzymes. The results are shown in Tables 7–9.

TABLE 7

Effect of Cofactors on 18:0-CoA Elongation[1]

| Gene | Expt[4] | +Glu[2] | +Gal[2] | − ATP[3] | − CoA[3] | − A&C[3] | + Cer[3] |
|---|---|---|---|---|---|---|---|
| EL1 | 1 | .037 | .109 | .095 | .105 | .119 | .141 |
|  | 2 | N.D. | .090 | .125 | .093 | .270 | .176 |
| EL2 | 1 | .033 | .112 | .168 | .127 | .143 | .238 |
|  | 2 | N.D. | .120 | .178 | .133 | .195 | .302 |

[1]Activity in nanomoles/minute/mg of microsomal protein.
[2]+Glu: microsomes from cultures grown in the presence of glucose and incubated in standard reaction mix; + Gal: microsomes from cultures grown in the presence of galactose and incubated in standard reaction mix.
[3]Microsomes from galactose-induced cultures. − ATP: ATP omitted from reaction mix; − CoA: Coenzyme A omitted from reaction mix; − A&C: ATP and Coenzyme A omitted from reaction mix; +Cer: Standard reaction mix containing 0.01 mM cerulenin.
[4]Experiment No.

TABLE 8

Effect of Cofactors on Elongation Products of EL1[1]

| Prod. | + Glu[2] | + Gal[2] | − ATP[3] | − CoA[3] | − A&C[3] | +Cer[3] |
|---|---|---|---|---|---|---|
| 20:0 | 53.9 | 46.2 | 34.4 | 47.8 | 41.7 | 46.7 |
| 22:0 | 14.4 | 18.7 | 13.7 | 18.0 | 19.4 | 16.2 |
| 24:0 | 18.5 | 18.1 | 20.6 | 19.1 | 16.7 | 17.7 |
| 26:0 | 13.2 | 17.1 | 31.4 | 15.2 | 22.3 | 19.4 |
| Total | 100.0 | 100.0 | 100.0 | 100.0 | 100.0 | 100.0 |

[1]Amount of indicated product as a percent of total products formed. Results of one experiment for + Glucose; Average of two experiments for other conditions.
[2]+ Glu: microsomes from cultures grown in the presence of glucose and incubated in standard reaction mix; + Gal: microsoines from cultures grown in the presence of galactose and incubated in standard reaction mix.
[3]Microsomes from galactose-induced cultures. − ATP: ATP omitted from reaction mix; − CoA: Coenzyme A omitted from reaction mix; − A&C: ATP and Coenzyme A omitted from reaction mix; +Cer: Standard reaction mix containing 0.01 mM cerulenin.

TABLE 9

Effect of Cofactors on Elongation Products of EL2[1]

| Prod. | + Glu[2] | + Gal[2] | − ATP[3] | − CoA[3] | − A&C[3] | +Cer[3] |
|---|---|---|---|---|---|---|
| 20:0 | 54.5 | 47.1 | 34.1 | 45.3 | 38.0 | 41.8 |
| 22:0 | 17.1 | 19.1 | 16.4 | 19.2 | 15.9 | 16.1 |
| 24:0 | 5.8 | 19.4 | 20.8 | 19.9 | 18.4 | 20.4 |
| 26:0 | 22.6 | 14.5 | 28.9 | 15.8 | 27.8 | 21.8 |
| Total | 100.0 | 100.0 | 100.0 | 100.0 | 100.0 | 100.0 |

[1]Amount of indicated product as a percent of total products formed. Results of one experiment for + Glucose; Average of two experiments for other conditions.
[2]+ Glu: microsomes from cultures grown in the presence of glucose and incubated in standard reaction mix; + Gal: microsomes from cultures grown in the presence of galactose and incubated in standard reaction mix.
[3]Microsomes from galactose-induced cultures. − ATP: ATP omitted from reaction mix; − CoA: Coenzyme A omitted from reaction mix; − A&C: ATP and Coenzyme A omitted from reaction mix; +Cer: Standard reaction mix containing 0.01 mM cerulenin.

The results in Table 7 indicate that omission of ATP and/or CoA from the incubation mixture does not have a significant effect on the overall amounts of VLCFAs synthesized by the in vitro KAS activity of EL1 or EL2. The results also show that cerulenin does not inhibit the KAS activity of EL1 or EL2. The data in Table 8 and 9 confirm that EL1 and EL2 KAS activity produces significant amounts of C24:0 and C26:0 acyl CoA products.

To the extent not already indicated, it will be understood by those of ordinary skill in the art that any one of the various specific embodiments herein described and illustrated may be further modified to incorporate features shown in other of the specific embodiments.

The foregoing detailed description has been provided for a better understanding of the invention only and no unnecessary limitation should be understood therefrom as some modifications will be apparent to those skilled in the art without deviating from the spirit and scope of the appended claims.

SEQUENCE LISTING

<160> NUMBER OF SEQ ID NOS: 22

<210> SEQ ID NO 1
<211> LENGTH: 1560
<212> TYPE: DNA
<213> ORGANISM: Arabidopsis thaliana

<400> SEQUENCE: 1

```
atggatcgag agagattaac ggcggagatg gcgtttcgag attcatcatc ggccgttata    60
agaattcgaa gacgtttgcc ggatttatta acgtccgtta agctcaaata cgtgaagctt   120
ggacttcaca actcttgcaa cgtgaccacc attctcttct tcttaattat tcttccttta   180
accggaaccg tgctggttca gctaaccggt ctaacgttcg atacgttctc tgagctttgg   240
tctaaccagg cggttcaact cgacacggcg acgagactta cctgcttggt tttcctctcc   300
ttcgttttga ccctctacgt ggctaaccgg tctaaaccgg tttacctagt ggatttctcc   360
tgctacaaac cggaagacga gcgtaaaata tcagtagatt cgttcttgac gatgactgag   420
```

-continued

```
gaaaatggat cattcaccga tgacacggtt cagttccagc aaagaatctc gaaccgggcc    480
ggtttgggag acgagacgta tctgccacgt ggcataactt caacgccccc gaagctaaat    540
atgtcagagg cacgtgccga agctgaagcc gttatgtttg agccttaga ttccctcttc     600 gagaaaaccg gaattaaacc ggccgaagtc ggaatcttga tagtaaactg cagcttattc    660
aatccgacgc cgtctctatc agcgatgatc gtgaaccatt acaagatgag agaagacatc    720
aaaagttaca acctcggagg aatgggttgc tccgccggat taatctcaat cgatctcgct    780
aacaatctcc tcaaagcaaa ccctaattct tacgctgtcg tggtaagcac ggaaaacata    840
accctaaact ggtacttcgg aaatgaccgg tcaatgctcc tctgcaactg catcttccga    900
atgggcggag ctgcgattct cctctctaac cgccgtcaag accggaagaa gtcaaagtac    960
tcgctggtca acgtcgttcg aacacataaa ggatcagacg acaagaacta caattgcgtg   1020
taccagaagg aagacgagag aggaacaatc ggtgtctctt tagctagaga gctcatgtct   1080
gtcgccggag acgctctgaa acaaacatc acgactttag gaccgatggt tcttccattg    1140
tcagagcagt tgatgttctt gatttccttg gtcaaaagga agatgttcaa gttaaaagtt   1200
aaaccgtata ttccggattt caagctagct ttcgagcatt tctgtattca cgcaggaggt   1260
agagcggttc tagacgaagt gcagaagaat cttgatctca aagattggca catggaacct   1320
tctagaatga ctttgcacag atttggtaac acttcgagta gctcgctttg gtatgagatg   1380
gcttataccg aagctaaggg tcgggttaaa gctggtgacc gactttggca gattgcgttt   1440
ggatcgggtt tcaagtgtaa tagtgcggtt tggaaagcgt tacgaccggt ttcgacggag   1500
gagatgaccg gtaatgcttg ggctggttcg attgatcaat atccggttaa agttgtgcaa   1560
```

<210> SEQ ID NO 2
<211> LENGTH: 520
<212> TYPE: PRT
<213> ORGANISM: Arabidopsis thaliana

<400> SEQUENCE: 2

```
Met Asp Arg Glu Arg Leu Thr Ala Glu Met Ala Phe Arg Asp Ser Ser
 1               5                  10                  15

Ser Ala Val Ile Arg Ile Arg Arg Leu Pro Asp Leu Leu Thr Ser
            20                  25                  30

Val Lys Leu Lys Tyr Val Lys Leu Gly Leu His Asn Ser Cys Asn Val
        35                  40                  45

Thr Thr Ile Leu Phe Phe Leu Ile Ile Leu Pro Leu Thr Gly Thr Val
    50                  55                  60

Leu Val Gln Leu Thr Gly Leu Thr Phe Asp Thr Phe Ser Glu Leu Trp
65                  70                  75                  80

Ser Asn Gln Ala Val Gln Leu Asp Thr Ala Thr Arg Leu Thr Cys Leu
                85                  90                  95

Val Phe Leu Ser Phe Val Leu Thr Leu Tyr Val Ala Asn Arg Ser Lys
            100                 105                 110

Pro Val Tyr Leu Val Asp Phe Ser Cys Tyr Lys Pro Asp Glu Arg
        115                 120                 125

Lys Ile Ser Val Asp Ser Phe Leu Thr Met Thr Glu Glu Asn Gly Ser
    130                 135                 140

Phe Thr Asp Asp Thr Val Gln Phe Gln Gln Arg Ile Ser Asn Arg Ala
145                 150                 155                 160

Gly Leu Gly Asp Glu Thr Tyr Leu Pro Arg Gly Ile Thr Ser Thr Pro
                165                 170                 175
```

Pro Lys Leu Asn Met Ser Glu Ala Arg Ala Glu Ala Val Met
        180                 185                 190

Phe Gly Ala Leu Asp Ser Leu Phe Glu Lys Thr Gly Ile Lys Pro Ala
        195                 200                 205

Glu Val Gly Ile Leu Ile Val Asn Cys Ser Leu Phe Asn Pro Thr Pro
    210                 215                 220

Ser Leu Ser Ala Met Ile Val Asn His Tyr Lys Met Arg Glu Asp Ile
225                 230                 235                 240

Lys Ser Tyr Asn Leu Gly Gly Met Gly Cys Ser Ala Gly Leu Ile Ser
                245                 250                 255

Ile Asp Leu Ala Asn Asn Leu Leu Lys Ala Asn Pro Asn Ser Tyr Ala
                260                 265                 270

Val Val Val Ser Thr Glu Asn Ile Thr Leu Asn Trp Tyr Phe Gly Asn
                275                 280                 285

Asp Arg Ser Met Leu Leu Cys Asn Cys Ile Phe Arg Met Gly Gly Ala
        290                 295                 300

Ala Ile Leu Leu Ser Asn Arg Arg Gln Asp Arg Lys Lys Ser Lys Tyr
305                 310                 315                 320

Ser Leu Val Asn Val Val Arg Thr His Lys Gly Ser Asp Asp Lys Asn
                325                 330                 335

Tyr Asn Cys Val Tyr Gln Lys Glu Asp Glu Arg Gly Thr Ile Gly Val
                340                 345                 350

Ser Leu Ala Arg Glu Leu Met Ser Val Ala Gly Asp Ala Leu Lys Thr
                355                 360                 365

Asn Ile Thr Thr Leu Gly Pro Met Val Leu Pro Leu Ser Glu Gln Leu
        370                 375                 380

Met Phe Leu Ile Ser Leu Val Lys Arg Lys Met Phe Lys Leu Lys Val
385                 390                 395                 400

Lys Pro Tyr Ile Pro Asp Phe Lys Leu Ala Phe Glu His Phe Cys Ile
                405                 410                 415

His Ala Gly Gly Arg Ala Val Leu Asp Glu Val Gln Lys Asn Leu Asp
                420                 425                 430

Leu Lys Asp Trp His Met Glu Pro Ser Arg Met Thr Leu His Arg Phe
        435                 440                 445

Gly Asn Thr Ser Ser Ser Leu Trp Tyr Glu Met Ala Tyr Thr Glu
        450                 455                 460

Ala Lys Gly Arg Val Lys Ala Gly Asp Arg Leu Trp Gln Ile Ala Phe
465                 470                 475                 480

Gly Ser Gly Phe Lys Cys Asn Ser Ala Val Trp Lys Ala Leu Arg Pro
                485                 490                 495

Val Ser Thr Glu Glu Met Thr Gly Asn Ala Trp Ala Gly Ser Ile Asp
                500                 505                 510

Gln Tyr Pro Val Lys Val Val Gln
        515                 520

<210> SEQ ID NO 3
<211> LENGTH: 1479
<212> TYPE: DNA
<213> ORGANISM: Arabidopsis thaliana

<400> SEQUENCE: 3
atggattacc ccatgaagaa ggtaaaaatc tttttcaact acctcatggc gcatcgcttc    60
aagctctgct tcttaccatt aatggttgct atagccgtgg aggcgtctcg tctttccaca   120

-continued

```
caagatctcc aaaacttta cctctactta caaaacaacc acacatctct aaccatgttc    180
ttcctttacc tcgctctcgg gtcgactctt tacctcatga cccggcccaa acccgtttat   240
ctcgttgact ttagctgcta cctcccaccg tcgcatctca aagccagcac ccagaggatc   300
atgcaacacg taaggcttgt acgagaagca ggcgcgtgga agcaagagtc cgattacttg   360
atggacttct gcgagaagat tctagaacgt tccggtctag gccaagagac gtacgtaccc   420
gaaggtcttc aaactttgcc actacaacag aatttggctg tatcacgtat agagacggag   480
gaagttatta ttggtgcggt cgataatctg tttcgcaaca cgggaataag ccctagtgat   540
ataggtatat tggtggtgaa ttcaagcact tttaatccaa caccttcgct atcaagtatc   600
ttagtgaata agtttaaact tagggataat ataaagagct tgaatcttgg tgggatgggg   660
tgtagcgctg gagtcatcgc tatcgatgcg gctaagagct tgttacaagt tcatagaaac   720
acttatgctc ttgtggtgag cacggagaac atcactcaaa acttgtacat gggtaacaac   780
aaatcaatgt tggttacaaa ctgtttgttc cgtataggtg gggccgcgat tttgctttct   840
aaccggtcta tagatcgtaa acgcgcaaaa tacgagcttg ttcacaccgt gcgggtccat   900
accggagcag atgaccgatc ctatgaatgt gcaactcaag aagaggatga agatggcata   960
gttgggggttt ccttgtcaaa gaatctacca atggtagctg caagaaccct aaagatcaat  1020
atcgcaactt tgggtccgct tgttcttccc ataagcgaga gtttcactt ctttgtgagg    1080
ttcgttaaaa agaagtttct caaccccaag ctaaagcatt acattccgga tttcaagctc   1140
gcattcgagc atttctgtat ccatgcgggt ggtagagcgc taattgatga gatggagaag   1200
aatcttcatc taactccact agacgttgag gcttcaagaa tgacattaca caggtttggt   1260
aatacctctt cgagctccat ttggtacgag ttggcttaca cagaagccaa aggaaggatg   1320
acgaaaggag ataggatttg gcagattgcg ttggggtcag gttttaagtg taatagttca   1380
gtttgggtgg ctcttcgtaa cgtcaagcct tctactaata atccttggga acagtgtcta   1440
cacaaatatc cagttgagat cgatatagat ttaaaagag                          1479
```

<210> SEQ ID NO 4
<211> LENGTH: 493
<212> TYPE: PRT
<213> ORGANISM: Arabidopsis thaliana

<400> SEQUENCE: 4

```
Met Asp Tyr Pro Met Lys Lys Val Lys Ile Phe Phe Asn Tyr Leu Met
 1               5                  10                  15

Ala His Arg Phe Lys Leu Cys Phe Leu Pro Leu Met Val Ala Ile Ala
                20                  25                  30

Val Glu Ala Ser Arg Leu Ser Thr Gln Asp Leu Gln Asn Phe Tyr Leu
            35                  40                  45

Tyr Leu Gln Asn Asn His Thr Ser Leu Thr Met Phe Phe Leu Tyr Leu
        50                  55                  60

Ala Leu Gly Ser Thr Leu Tyr Leu Met Thr Arg Pro Lys Pro Val Tyr
 65                  70                  75                  80

Leu Val Asp Phe Ser Cys Tyr Leu Pro Pro Ser His Leu Lys Ala Ser
                85                  90                  95

Thr Gln Arg Ile Met Gln His Val Arg Leu Val Arg Glu Ala Gly Ala
               100                 105                 110

Trp Lys Gln Glu Ser Asp Tyr Leu Met Asp Phe Cys Glu Lys Ile Leu
           115                 120                 125

Glu Arg Ser Gly Leu Gly Gln Glu Thr Tyr Val Pro Glu Gly Leu Gln
```

```
        130                 135                 140
Thr Leu Pro Leu Gln Gln Asn Leu Ala Val Ser Arg Ile Glu Thr Glu
145                 150                 155                 160
Glu Val Ile Ile Gly Ala Val Asp Asn Leu Phe Arg Asn Thr Gly Ile
                165                 170                 175
Ser Pro Ser Asp Ile Gly Ile Leu Val Val Asn Ser Ser Thr Phe Asn
            180                 185                 190
Pro Thr Pro Ser Leu Ser Ser Ile Leu Val Asn Lys Phe Lys Leu Arg
        195                 200                 205
Asp Asn Ile Lys Ser Leu Asn Leu Gly Gly Met Gly Cys Ser Ala Gly
    210                 215                 220
Val Ile Ala Ile Asp Ala Ala Lys Ser Leu Leu Gln Val His Arg Asn
225                 230                 235                 240
Thr Tyr Ala Leu Val Val Ser Thr Glu Asn Ile Thr Gln Asn Leu Tyr
                245                 250                 255
Met Gly Asn Asn Lys Ser Met Leu Val Thr Asn Cys Leu Phe Arg Ile
            260                 265                 270
Gly Gly Ala Ala Ile Leu Leu Ser Asn Arg Ser Ile Asp Arg Lys Arg
        275                 280                 285
Ala Lys Tyr Glu Leu Val His Thr Val Arg Val His Thr Gly Ala Asp
    290                 295                 300
Asp Arg Ser Tyr Glu Cys Ala Thr Gln Glu Glu Asp Glu Asp Gly Ile
305                 310                 315                 320
Val Gly Val Ser Leu Ser Lys Asn Leu Pro Met Val Ala Ala Arg Thr
                325                 330                 335
Leu Lys Ile Asn Ile Ala Thr Leu Gly Pro Leu Val Leu Pro Ile Ser
            340                 345                 350
Glu Lys Phe His Phe Val Arg Phe Val Lys Lys Phe Leu Asn
        355                 360                 365
Pro Lys Leu Lys His Tyr Ile Pro Asp Phe Lys Leu Ala Phe Glu His
    370                 375                 380
Phe Cys Ile His Ala Gly Gly Arg Ala Leu Ile Asp Glu Met Glu Lys
385                 390                 395                 400
Asn Leu His Leu Thr Pro Leu Asp Val Glu Ala Ser Arg Met Thr Leu
                405                 410                 415
His Arg Phe Gly Asn Thr Ser Ser Ser Ile Trp Tyr Glu Leu Ala
            420                 425                 430
Tyr Thr Glu Ala Lys Gly Arg Met Thr Lys Gly Asp Arg Ile Trp Gln
        435                 440                 445
Ile Ala Leu Gly Ser Gly Phe Lys Cys Asn Ser Ser Val Trp Val Ala
    450                 455                 460
Leu Arg Asn Val Lys Pro Ser Thr Asn Pro Trp Glu Gln Cys Leu
465                 470                 475                 480
His Lys Tyr Pro Val Glu Ile Asp Ile Asp Leu Lys Glu
                485                 490

<210> SEQ ID NO 5
<211> LENGTH: 1512
<212> TYPE: DNA
<213> ORGANISM: Arabidopsis thaliana

<400> SEQUENCE: 5
ctacgtcagg gtagaacaaa gagtaaacac ttaagcaaaa caatttgtcc tactcttagg      60
ttatctccaa tgaagaactt aaagatggtt ttcttcaaga tcctctttat ctctttaatg     120
```

```
gcaggattag ccatgaaagg atctaagatc aacgtagaag atctccaaaa gttctccctc    180
caccatacac agaacaacct ccaaaccata agccttctat tgtttcttgt cgttttttgtg   240 tggatcctct acatgttaac ccgacctaaa cccgtttacc ttgttgattt ctcctgctac    300
cttccaccgt cgcatctcaa ggtcagtatc caaaccctaa tgggacacgc aagacgtgca    360
agagaagcag gcatgtgttg aagaacaaa gagagcgacc atttagttga cttccaggag     420
aagattcttg aacgttccgg tcttggtcaa gaaacctaca tccccgaggg tcttcagtgc    480
ttcccacttc agcaaggcat gggtgcttca cgtaaagaga cggaagaagt aatcttcgga   540
gctcttgaca atcttttcg caacaccggt gtaaaacctg atgatatcgg tatattggtg    600
gtgaattcta gcacgtttaa tccaactcca tcactcgcct ccatgattgt gaacaagtac    660
aaactcagag acaacatcaa gagtttgaat cttggaggga tgggttgcag tgccggagtt    720
atagctgttg atgtcgctaa gggattacta caagttcata ggaacactta tgctattgta    780
gtaagcacag agaacatcac tcagaactta tacttgggga aaaacaaatc aatgctagtc    840
acaaactgtt tgttccgcgt tggtggtgct gcggttctgc tttcaaacag atctagagac    900
cgtaaccgcg ccaaatacga gcttgttcac accgtacgga tccataccgg atcagatgat   960
aggtcgttcg aatgtgcgac acaagaagag gatgaagatg gtataattgg agttaccttg   1020
acaaagaatc tacctatggg ggctgcaagg actcttaaga taaatatcgc aactttgggt  1080
cctcttgtac ttccattaaa agagaagcta gccttcttta ttacttttgt caagaagaag   1140
tatttcaagc cagagttaag gaattataca ccagatttca agcttgcctt tgagcatttc   1200
tgtatccacg ctggtggaag agctctaata gatgagctgg agaagaacct taagctttct   1260
ccgttacacg tagaggcgtc aagaatgaca ctacacaggt ttggtaacac ttcttctagc   1320
tcaatctggt acgagttagc ttatacagaa gctaaaggaa ggatgaagga aggagatagg   1380
atttggcaga ttgctttggg gtcaggtttt aagtgtaaca gttcagtatg ggtggctctg   1440
cgagacgtta agccttcagc taacagtcca tgggaagact gtatggatag atatccggtt   1500
gagattgata tt                                                        1512

<210> SEQ ID NO 6
<211> LENGTH: 504
<212> TYPE: PRT
<213> ORGANISM: Arabidopsis thaliana

<400> SEQUENCE: 6

Leu Arg Gln Gly Arg Thr Lys Ser Lys His Leu Ser Lys Thr Ile Cys
 1               5                  10                  15

Pro Thr Leu Arg Leu Ser Pro Met Lys Asn Leu Lys Met Val Phe Phe
             20                  25                  30

Lys Ile Leu Phe Ile Ser Leu Met Ala Gly Leu Ala Met Lys Gly Ser
         35                  40                  45

Lys Ile Asn Val Glu Asp Leu Gln Lys Phe Ser Leu His His Thr Gln
     50                  55                  60

Asn Asn Leu Gln Thr Ile Ser Leu Leu Phe Leu Val Val Phe Val
 65                  70                  75                  80

Trp Ile Leu Tyr Met Leu Thr Arg Pro Lys Pro Val Tyr Leu Val Asp
                 85                  90                  95

Phe Ser Cys Tyr Leu Pro Pro Ser His Leu Lys Val Ser Ile Gln Thr
            100                 105                 110

Leu Met Gly His Ala Arg Arg Ala Arg Glu Ala Gly Met Cys Trp Lys
```

```
            115                 120                 125
Asn Lys Glu Ser Asp His Leu Val Asp Phe Gln Glu Lys Ile Leu Glu
            130                 135                 140
Arg Ser Gly Leu Gly Gln Glu Thr Tyr Ile Pro Glu Gly Leu Gln Cys
145                 150                 155                 160
Phe Pro Leu Gln Gln Gly Met Gly Ala Ser Arg Lys Glu Thr Glu Glu
                    165                 170                 175
Val Ile Phe Gly Ala Leu Asp Asn Leu Phe Arg Asn Thr Gly Val Lys
                180                 185                 190
Pro Asp Asp Ile Gly Ile Leu Val Val Asn Ser Ser Thr Phe Asn Pro
                195                 200                 205
Thr Pro Ser Leu Ala Ser Met Ile Val Asn Lys Tyr Lys Leu Arg Asp
            210                 215                 220
Asn Ile Lys Ser Leu Asn Leu Gly Gly Met Gly Cys Ser Ala Gly Val
225                 230                 235                 240
Ile Ala Val Asp Val Ala Lys Gly Leu Leu Gln Val His Arg Asn Thr
                    245                 250                 255
Tyr Ala Ile Val Val Ser Thr Glu Asn Ile Thr Gln Asn Leu Tyr Leu
                260                 265                 270
Gly Lys Asn Lys Ser Met Leu Val Thr Asn Cys Leu Phe Arg Val Gly
                275                 280                 285
Gly Ala Ala Val Leu Leu Ser Asn Arg Ser Arg Asp Arg Asn Arg Ala
            290                 295                 300
Lys Tyr Glu Leu Val His Thr Val Arg Ile His Thr Gly Ser Asp Asp
305                 310                 315                 320
Arg Ser Phe Glu Cys Ala Thr Gln Glu Glu Asp Glu Asp Gly Ile Ile
                    325                 330                 335
Gly Val Thr Leu Thr Lys Asn Leu Pro Met Val Ala Ala Arg Thr Leu
                340                 345                 350
Lys Ile Asn Ile Ala Thr Leu Gly Pro Leu Val Leu Pro Leu Lys Glu
                355                 360                 365
Lys Leu Ala Phe Phe Ile Thr Phe Val Lys Lys Tyr Phe Lys Pro
            370                 375                 380
Glu Leu Arg Asn Tyr Thr Pro Asp Phe Lys Leu Ala Phe Glu His Phe
385                 390                 395                 400
Cys Ile His Ala Gly Gly Arg Ala Leu Ile Asp Glu Leu Glu Lys Asn
                    405                 410                 415
Leu Lys Leu Ser Pro Leu His Val Glu Ala Ser Arg Met Thr Leu His
                420                 425                 430
Arg Phe Gly Asn Thr Ser Ser Ser Ile Trp Tyr Glu Leu Ala Tyr
            435                 440                 445
Thr Glu Ala Lys Gly Arg Met Lys Glu Gly Asp Arg Ile Trp Gln Ile
450                 455                 460
Ala Leu Gly Ser Gly Phe Lys Cys Asn Ser Ser Val Trp Val Ala Leu
465                 470                 475                 480
Arg Asp Val Lys Pro Ser Ala Asn Ser Pro Trp Glu Asp Cys Met Asp
                    485                 490                 495
Arg Tyr Pro Val Glu Ile Asp Ile
                500

<210> SEQ ID NO 7
<211> LENGTH: 1650
<212> TYPE: DNA
<213> ORGANISM: Arabidopsis thaliana
```

<400> SEQUENCE: 7

```
atgggtagat ccaacgagca agatctgctc tctaccgaga tcgttaatcg tgggatcgaa        60
ccatccggtc ctaacgccgg ctcaccaacg ttctcggtta gggtcaggag acgtttgcct       120
gattttcttc agtcggtgaa cttgaagtac gtgaaacttg gttaccacta cctcataaac       180
catgcggttt atttggcgac ataccggttc ttgtgctggt ttttagtgc tgaggttggg        240
agtttaagca gagaagagat ttggaagaag ctttgggact atgatcttgc aactgttatc       300
ggattcttcg gtgtctttgt tttaaccgct tgtgtctact tcatgtctcg tcctcgctct       360
gtttatctta ttgatttcgc ttgttacaag ccctccgatg aacacaaggt gacaaaagaa       420
gagttcatag aactagcgag aaaatcaggg aagttcgacg aagagacact cggtttcaag       480
aagaggatct acaagcctc aggcataggc gacgagacat cgtcccaag atccatctct         540
tcatcagaaa acataacaac gatgaaagaa ggtcgtgaag aagcctctac agtgatcttt       600
ggagcactag acgaactctt cgagaagaca cgtgtaaaac ctaaagacgt tggtgtcctt       660
gtggttaact gtagcatttt caaccccgaca ccgtcgttgt ccgcaatggt gataaaccat      720
tacaagatga gagggaacat acttagttac aaccttggag ggatgggatg ttcggctgga       780
atcatagcta ttgatcttgc tcgtgacatg cttcagtcta accctaatag ttatgctgtt       840
gttgtgagta ctgagatggt tgggtataat tggtacgtgg aagtgacaa gtcaatggtt        900
atacctaatt gtttctttag gatgggttgt tctgccgtta tgctctctaa ccgtcgtcgt       960
gactttcgcc atgctaagta ccgtctcgag cacattgtcc gaactcataa ggctgctgac      1020
gaccgtagct tcaggagtgt gtaccaggaa gaagatgaac aaggattcaa ggggttgaag      1080
ataagtagag acttaatgga agttggaggt gaagctctca agacaaacat cactacctta      1140
ggtcctcttg tcctaccttt ctccgagcag cttctcttct ttgctgcttt ggtccgccga      1200
acattctcac ctgctgccaa acgtccaca accacttcct tctctacttc cgccaccgca      1260
aaaaccaatg gaatcaagtc ttcctcttcc gatctgtcca agccatacat cccggactac      1320
aagctcgcct tcgagcattt ttgcttccac gcggcaagca agtagtgct tgaagagctt       1380
caaaagaatc taggcttgag tgaagagaat atggaggctt ctaggatgac acttcacagg      1440
tttggaaaca cttctagcag tggaatctgg tatgagttgc cttacatgga ggccaaggaa      1500
agtgttcgta gaggcgatag ggtttggcag atcgctttcg gttctggttt taagtgtaac      1560
agtgtggtgt ggaaggcaat gaggaaggtg aagaagccaa ccaggaacaa tccttgggtg      1620
gattgcatca accgttaccc tgtgcctctc                                       1650
```

<210> SEQ ID NO 8
<211> LENGTH: 550
<212> TYPE: PRT
<213> ORGANISM: Arabidopsis thaliana

<400> SEQUENCE: 8

```
Met Gly Arg Ser Asn Glu Gln Asp Leu Leu Ser Thr Glu Ile Val Asn
 1               5                  10                  15

Arg Gly Ile Glu Pro Ser Gly Pro Asn Ala Gly Ser Pro Thr Phe Ser
            20                  25                  30

Val Arg Val Arg Arg Arg Leu Pro Asp Phe Leu Gln Ser Val Asn Leu
        35                  40                  45

Lys Tyr Val Lys Leu Gly Tyr His Tyr Leu Ile Asn His Ala Val Tyr
    50                  55                  60
```

-continued

```
Leu Ala Thr Ile Pro Val Leu Val Leu Val Phe Ser Ala Glu Val Gly
 65                  70                  75                  80

Ser Leu Ser Arg Glu Glu Ile Trp Lys Lys Leu Trp Asp Tyr Asp Leu
                 85                  90                  95

Ala Thr Val Ile Gly Phe Phe Gly Val Phe Val Leu Thr Ala Cys Val
                100                 105                 110

Tyr Phe Met Ser Arg Pro Arg Ser Val Tyr Leu Ile Asp Phe Ala Cys
            115                 120                 125

Tyr Lys Pro Ser Asp Glu His Lys Val Thr Lys Glu Glu Phe Ile Glu
        130                 135                 140

Leu Ala Arg Lys Ser Gly Lys Phe Asp Glu Thr Leu Gly Phe Lys
145                 150                 155                 160

Lys Arg Ile Leu Gln Ala Ser Gly Ile Gly Asp Glu Thr Tyr Val Pro
                165                 170                 175

Arg Ser Ile Ser Ser Ser Glu Asn Ile Thr Thr Met Lys Glu Gly Arg
            180                 185                 190

Glu Glu Ala Ser Thr Val Ile Phe Gly Ala Leu Asp Glu Leu Phe Glu
        195                 200                 205

Lys Thr Arg Val Lys Pro Lys Asp Val Gly Val Leu Val Asn Cys
210                 215                 220

Ser Ile Phe Asn Pro Thr Pro Ser Leu Ser Ala Met Val Ile Asn His
225                 230                 235                 240

Tyr Lys Met Arg Gly Asn Ile Leu Ser Tyr Asn Leu Gly Gly Met Gly
                245                 250                 255

Cys Ser Ala Gly Ile Ile Ala Ile Asp Leu Ala Arg Asp Met Leu Gln
            260                 265                 270

Ser Asn Pro Asn Ser Tyr Ala Val Val Ser Thr Glu Met Val Gly
        275                 280                 285

Tyr Asn Trp Tyr Val Gly Ser Asp Lys Ser Met Val Ile Pro Asn Cys
290                 295                 300

Phe Phe Arg Met Gly Cys Ser Ala Val Met Leu Ser Asn Arg Arg
305                 310                 315                 320

Asp Phe Arg His Ala Lys Tyr Arg Leu Glu His Ile Val Arg Thr His
                325                 330                 335

Lys Ala Ala Asp Asp Arg Ser Phe Arg Ser Val Tyr Gln Glu Glu Asp
            340                 345                 350

Glu Gln Gly Phe Lys Gly Leu Lys Ile Ser Arg Asp Leu Met Glu Val
        355                 360                 365

Gly Gly Glu Ala Leu Lys Thr Asn Ile Thr Thr Leu Gly Pro Leu Val
370                 375                 380

Leu Pro Phe Ser Glu Gln Leu Leu Phe Phe Ala Ala Leu Val Arg Arg
385                 390                 395                 400

Thr Phe Ser Pro Ala Ala Lys Thr Ser Thr Thr Thr Ser Phe Ser Thr
                405                 410                 415

Ser Ala Thr Ala Lys Thr Asn Gly Ile Lys Ser Ser Ser Ser Asp Leu
            420                 425                 430

Ser Lys Pro Tyr Ile Pro Asp Tyr Lys Leu Ala Phe Glu His Phe Cys
        435                 440                 445

Phe His Ala Ala Ser Lys Val Val Leu Glu Glu Leu Gln Lys Asn Leu
        450                 455                 460

Gly Leu Ser Glu Glu Asn Met Glu Ala Ser Arg Met Thr Leu His Arg
465                 470                 475                 480

Phe Gly Asn Thr Ser Ser Ser Gly Ile Trp Tyr Glu Leu Ala Tyr Met
```

```
            485                 490                 495
Glu Ala Lys Glu Ser Val Arg Arg Gly Asp Arg Val Trp Gln Ile Ala
            500                 505                 510

Phe Gly Ser Gly Phe Lys Cys Asn Ser Val Val Trp Lys Ala Met Arg
            515                 520                 525

Lys Val Lys Lys Pro Thr Arg Asn Asn Pro Trp Val Asp Cys Ile Asn
            530                 535                 540

Arg Tyr Pro Val Pro Leu
545             550

<210> SEQ ID NO 9
<211> LENGTH: 1611
<212> TYPE: DNA
<213> ORGANISM: Arabidopsis thaliana

<400> SEQUENCE: 9
tcgagctacg tcagggcttt tatatgcaca aattctcata aagttttcaa ttttattcca      60
tttttctcgg aagccatgga agctgctaat gagcctgtta atggcggatc cgtacagatc     120
cgaacagaga acaacgaaag acgaaagctt cctaatttct acaaagcgt caacatgaaa      180 tacgtcaagc taggttatca ttacctcatt actcatctct tcaagctctg tttggttcca     240
ttaatggcgg ttttagtcac agagatctct cgattaacaa cagacgatct ttaccagatt     300
tggcttcatc tccaatacaa tctcgttgct ttcatctttc tctctgcttt agctatcttt     360
ggctccaccg tttacatcat gagtcgtccc agatctgttt atctcgttga ttactcttgt     420
tatcttcctc cggagagtct tcaggttaag tatcagaagt ttatggatca ttctaagttg     480
attgaagatt tcaatgagtc atctttagag tttcagagga agattcttga acgttctggt     540
ttaggagaag agacttatct ccctgaagct ttacattgta ccctccgag gcctacgatg      600 atggcggctc gtgaggaatc tgagcaggta atgtttggtg ctcttgataa gcttttcgag     660
aataccaaga ttaaccctag ggatattggt gtgttggttg tgaattgtag cttgtttaat     720
cctacacctt cgttgtcagc tatgattgtt aacaagtata agcttagagg gaatgttaag     780
agttttaacc ttggtggaat ggggtgtagt gctggtgtta tctctatcga tttagctaaa     840
gatatgttgc aagttcatag gaatacttat gctgttgtgg ttagtactga gaacattact     900
cagaattggt attttgggaa taagaaggct atgttgattc cgaattgttt gtttcgtgtt     960
ggtggttcgg cgattttgtt gtcgaacaag gggaaagatc gtagacggtc taagtataag    1020
cttgttcata ccgttaggac tcataaagga gctgttgaga aggctttcaa ctgtgtttac    1080
caagagcaag atgataatgg gaagaccggg gtttcgttgt cgaaagatct tatggctata    1140
gctggggaag ctcttaaggc gaatatcact actttaggtc ctttggttct tcctataagt    1200
gagcagattc tgttttcat gactttggtt acgaagaaac tgtttaactc gaagctgaag     1260
ccgtatattc cggatttcaa gcttgcgttt gatcatttct gtatccatgc tggtggtaga    1320
gctgtgattg atgagcttga aagaatctg cagctttcgc agactcatgt cgaggcatcc     1380
agaatgacac tgcacagatt tggaaacact tcttcgagct cgatttggta tgaactggct    1440
tacatagagg ctaaaggtag gatgaagaaa ggaaaccggg tttggcagat tgcttttgga    1500
agtgggttta agtgtaacag tgcagtttgg gtggctctaa acaatgtcaa gccttcggtt    1560
agtagtccgt gggaacactg catcgaccga tatccggtta agctcgactt c             1611

<210> SEQ ID NO 10
<211> LENGTH: 537
```

<212> TYPE: PRT
<213> ORGANISM: Arabidopsis thaliana

<400> SEQUENCE: 10

```
Ser Ser Tyr Val Arg Ala Phe Ile Cys Thr Asn Ser His Lys Val Phe
  1               5                  10                  15
Asn Phe Ile Pro Phe Phe Ser Glu Ala Met Glu Ala Ala Asn Glu Pro
             20                  25                  30
Val Asn Gly Gly Ser Val Gln Ile Arg Thr Glu Asn Asn Glu Arg Arg
         35                  40                  45
Lys Leu Pro Asn Phe Leu Gln Ser Val Asn Met Lys Tyr Val Lys Leu
 50                  55                  60
Gly Tyr His Tyr Leu Ile Thr His Leu Phe Lys Leu Cys Leu Val Pro
 65                  70                  75                  80
Leu Met Ala Val Leu Val Thr Glu Ile Ser Arg Leu Thr Thr Asp Asp
                 85                  90                  95
Leu Tyr Gln Ile Trp Leu His Leu Gln Tyr Asn Leu Val Ala Phe Ile
                100                 105                 110
Phe Leu Ser Ala Leu Ala Ile Phe Gly Ser Thr Val Tyr Ile Met Ser
            115                 120                 125
Arg Pro Arg Ser Val Tyr Leu Val Asp Tyr Ser Cys Tyr Leu Pro Pro
130                 135                 140
Glu Ser Leu Gln Val Lys Tyr Gln Lys Phe Met Asp His Ser Lys Leu
145                 150                 155                 160
Ile Glu Asp Phe Asn Glu Ser Ser Leu Glu Phe Gln Arg Lys Ile Leu
                165                 170                 175
Glu Arg Ser Gly Leu Gly Glu Glu Thr Tyr Leu Pro Glu Ala Leu His
            180                 185                 190
Cys Ile Pro Pro Arg Pro Thr Met Met Ala Ala Arg Glu Glu Ser Glu
            195                 200                 205
Gln Val Met Phe Gly Ala Leu Asp Lys Leu Phe Glu Asn Thr Lys Ile
        210                 215                 220
Asn Pro Arg Asp Ile Gly Val Leu Val Asn Cys Ser Leu Phe Asn
225                 230                 235                 240
Pro Thr Pro Ser Leu Ser Ala Met Ile Val Asn Lys Tyr Lys Leu Arg
                245                 250                 255
Gly Asn Val Lys Ser Phe Asn Leu Gly Gly Met Gly Cys Ser Ala Gly
            260                 265                 270
Val Ile Ser Ile Asp Leu Ala Lys Asp Met Leu Gln Val His Arg Asn
        275                 280                 285
Thr Tyr Ala Val Val Ser Thr Glu Asn Ile Thr Gln Asn Trp Tyr
        290                 295                 300
Phe Gly Asn Lys Lys Ala Met Leu Ile Pro Asn Cys Leu Phe Arg Val
305                 310                 315                 320
Gly Gly Ser Ala Ile Leu Leu Ser Asn Lys Gly Lys Asp Arg Arg Arg
                325                 330                 335
Ser Lys Tyr Lys Leu Val His Thr Val Arg Thr His Lys Gly Ala Val
                340                 345                 350
Glu Lys Ala Phe Asn Cys Val Tyr Gln Glu Gln Asp Asp Asn Gly Lys
            355                 360                 365
Thr Gly Val Ser Leu Ser Lys Asp Leu Met Ala Ile Ala Gly Glu Ala
        370                 375                 380
Leu Lys Ala Asn Ile Thr Thr Leu Gly Pro Leu Val Leu Pro Ile Ser
385                 390                 395                 400
```

Glu Gln Ile Leu Phe Phe Met Thr Leu Val Thr Lys Lys Leu Phe Asn
                405                 410                 415

Ser Lys Leu Lys Pro Tyr Ile Pro Asp Phe Lys Leu Ala Phe Asp His
            420                 425                 430

Phe Cys Ile His Ala Gly Gly Arg Ala Val Ile Asp Glu Leu Glu Lys
            435                 440                 445

Asn Leu Gln Leu Ser Gln Thr His Val Glu Ala Ser Arg Met Thr Leu
        450                 455                 460

His Arg Phe Gly Asn Thr Ser Ser Ser Ile Trp Tyr Glu Leu Ala
465                 470                 475                 480

Tyr Ile Glu Ala Lys Gly Arg Met Lys Lys Gly Asn Arg Val Trp Gln
                485                 490                 495

Ile Ala Phe Gly Ser Gly Phe Lys Cys Asn Ser Ala Val Trp Val Ala
            500                 505                 510

Leu Asn Val Lys Pro Ser Val Ser Ser Pro Trp Glu His Cys Ile
        515                 520                 525

Asp Arg Tyr Pro Val Lys Leu Asp Phe
    530                 535

<210> SEQ ID NO 11
<211> LENGTH: 1502
<212> TYPE: DNA
<213> ORGANISM: Arabidopsis thaliana

<400> SEQUENCE: 11
tctccgacga tgcctcaggc accgatgcca gagttctcta gctcggtgaa gctcaagtac    60
gtgaaacttg gttaccaata tttggttaac catttcttga gttttctttt gatcccgatc   120
atggctattg tcgccgttga gcttcttcgg atgggtcctg aagagatcct taatgtttgg   180 aatttcactcc agtttgacct agttcaggtt ctatgttctt ccttctttgt catcttcatc   240
tccactgttt acttcatgtc aagccacgc accatctacc tcgttgacta ttcttgttac   300
aagccacctg tcacgtgtcg tgtccccttc gcaactttca tggaacactc tcgtttgatc   360
ctcaaggaca agcctaagag cgtcgagttc caaatgagaa tccttgaacg ttctggcctc   420
ggtgaggaga cttgtctccc tccggctatt cattatattc ctcccacacc aaccatggac   480
gcggctagaa gcgaggctca gatggttatc ttcgaggcca tggacgatct tttcaagaaa   540
accggtctta aacctaaaga cgtcgacatc cttatcgtca actgctctct tttctctccc   600
acaccatcgc tctcagctat ggtcatcaac aaatataagc ttaggagtaa tatcaagagc   660
ttcaatcttt cggggatggg ctgcagcgcg ggcctgatct cagttgatct agcccgcgac   720
ttgctccaag ttcatcccaa ttcaaatgca atcatcgtca gcacggagat cataacgcct   780
aattactatc aaggcaacga gagagccatg ttgttaccca attgtctctt ccgcatgggt   840
gcggcagcca tacacatgtc aaaccgccgg tctgaccggt ggcgagccaa atacaagctt   900
tcccacctcg tccggacaca ccgtggcgct gacgacaagt cttttctactg tgtctacgaa   960 caggaagaca agaaggaca cgttggcatc aacttgtcca agatctcat ggccatcgcc   1020 ggtgaagccc tcaaggcaaa catcaccaca ataggtcctt tggtcctacc ggcgtcagaa   1080
caacttctct tcctcacgtc cctaatcgga cgtaaaatct caacccgaa atggaaacca   1140 tacataccgg atttcaagct ggccttcgaa cacttttgca ttcacgcagg aggcagagcg   1200
gtgatcgacg agctccaaaa gaatctacaa ctatcaggag aacacgttga ggcctcaaga   1260
atgacactac atcgttttgg taacacgtca tcttcatcgt tatggtacga gcttagctac   1320

-continued

```
atcgagtcta aagggagaat gaggagaggc gatcgcgttt ggcaaatcgc gtttgggagt      1380
ggtttcaagt gtaactctgc cgtgtggaag tgtaaccgta cgattaagac acctaaggac      1440
ggaccatggt ccgattgtat cgaccgttac cctgtcttta ttcccgaagt tgtcaaactc      1500
ta                                                                     1502
```

<210> SEQ ID NO 12
<211> LENGTH: 500
<212> TYPE: PRT
<213> ORGANISM: Arabidopsis thaliana

<400> SEQUENCE: 12

```
Ser Pro Thr Met Pro Gln Ala Pro Met Pro Glu Phe Ser Ser Val
 1               5                  10                  15

Lys Leu Lys Tyr Val Lys Leu Gly Tyr Gln Tyr Leu Val Asn His Phe
             20                  25                  30

Leu Ser Phe Leu Leu Ile Pro Ile Met Ala Ile Val Ala Val Glu Leu
         35                  40                  45

Leu Arg Met Gly Pro Glu Glu Ile Leu Asn Val Trp Asn Ser Leu Gln
     50                  55                  60

Phe Asp Leu Val Gln Val Leu Cys Ser Ser Phe Phe Val Ile Phe Ile
 65                  70                  75                  80

Ser Thr Val Tyr Phe Met Ser Lys Pro Arg Thr Ile Tyr Leu Val Asp
                 85                  90                  95

Tyr Ser Cys Tyr Lys Pro Pro Val Thr Cys Arg Val Pro Phe Ala Thr
            100                 105                 110

Phe Met Glu His Ser Arg Leu Ile Leu Lys Asp Lys Pro Lys Ser Val
        115                 120                 125

Glu Phe Gln Met Arg Ile Leu Glu Arg Ser Gly Leu Gly Glu Glu Thr
    130                 135                 140

Cys Leu Pro Pro Ala Ile His Tyr Ile Pro Pro Thr Pro Thr Met Asp
145                 150                 155                 160

Ala Ala Arg Ser Glu Ala Gln Met Val Ile Phe Glu Ala Met Asp Asp
                165                 170                 175

Leu Phe Lys Lys Thr Gly Leu Lys Pro Lys Asp Val Asp Ile Leu Ile
            180                 185                 190

Val Asn Cys Ser Leu Phe Ser Pro Thr Pro Ser Leu Ser Ala Met Val
        195                 200                 205

Ile Asn Lys Tyr Lys Leu Arg Ser Asn Ile Lys Ser Phe Asn Leu Ser
    210                 215                 220

Gly Met Gly Cys Ser Ala Gly Leu Ile Ser Val Asp Leu Ala Arg Asp
225                 230                 235                 240

Leu Leu Gln Val His Pro Asn Ser Asn Ala Ile Ile Val Ser Thr Glu
                245                 250                 255

Ile Ile Thr Pro Asn Tyr Tyr Gln Gly Asn Glu Arg Ala Met Leu Leu
            260                 265                 270

Pro Asn Cys Leu Phe Arg Met Gly Ala Ala Ile His Met Ser Asn
        275                 280                 285

Arg Arg Ser Asp Arg Trp Arg Ala Lys Tyr Lys Leu Ser His Leu Val
    290                 295                 300

Arg Thr His Arg Gly Ala Asp Asp Lys Ser Phe Tyr Cys Val Tyr Glu
305                 310                 315                 320

Gln Glu Asp Lys Glu Gly His Val Gly Ile Asn Leu Ser Lys Asp Leu
                325                 330                 335
```

```
Met Ala Ile Ala Gly Glu Ala Leu Lys Ala Asn Ile Thr Thr Ile Gly
            340                 345                 350
Pro Leu Val Leu Pro Ala Ser Glu Gln Leu Leu Phe Leu Thr Ser Leu
        355                 360                 365
Ile Gly Arg Lys Ile Phe Asn Pro Lys Trp Lys Pro Tyr Ile Pro Asp
    370                 375                 380
Phe Lys Leu Ala Phe Glu His Phe Cys Ile His Ala Gly Gly Arg Ala
385                 390                 395                 400
Val Ile Asp Glu Leu Gln Lys Asn Leu Gln Leu Ser Gly Glu His Val
                405                 410                 415
Glu Ala Ser Arg Met Thr Leu His Arg Phe Gly Asn Thr Ser Ser Ser
            420                 425                 430
Ser Leu Trp Tyr Glu Leu Ser Tyr Ile Glu Ser Lys Gly Arg Met Arg
        435                 440                 445
Arg Gly Asp Arg Val Trp Gln Ile Ala Phe Gly Ser Gly Phe Lys Cys
    450                 455                 460
Asn Ser Ala Val Trp Lys Cys Asn Arg Thr Ile Lys Thr Pro Lys Asp
465                 470                 475                 480
Gly Pro Trp Ser Asp Cys Ile Asp Arg Tyr Pro Val Phe Ile Pro Glu
                485                 490                 495
Val Val Lys Leu
        500

<210> SEQ ID NO 13
<211> LENGTH: 1548
<212> TYPE: DNA
<213> ORGANISM: Arabidopsis thaliana

<400> SEQUENCE: 13
atggacggtg ccggagaatc acgactcggt ggtgatggtg gtggtgatgg ttctgttgga      60
gttcagatcc gacaaacacg gatgctaccg gattttctcc agagcgtgaa tctcaagtat     120
gtgaaattag gttaccatta cttaatctca aatctcttga ctctctgttt attccctctc     180
gccgttgtta tctccgtcga agcctctcag atgaacccag atgatctcaa acagctctgg     240
atccatctac aatacaatct ggttagtatc atcatctgtt cagcgattct agtcttcggg     300
ttaacggttt atgttatgac ccgacctaga cccgtttact tggttgattt ctcttgttat     360
ctcccacctg atcatctcaa agctccttac gctcggttca tggaacattc tagactcacc     420
ggagatttcg atgactctgc tctcgagttt caacgcaaga tccttgagcg ttctggttta     480
ggggaagaca cttatgtccc tgaagctatg cattatgttc caccgagaat ttcaatggct     540
gctgctagag aagaagctga acaagtcatg tttggtgctt tagataacct tttcgctaac     600
actaatgtga aaccaaagga tattggaatc cttgttgtga attgtagtct ctttaatcca     660
actccttcgt tatctgcaat gattgtgaac aagtataagc ttagaggtaa cattagaagc     720
tacaatctag gcggtatggg ttgcagcgcg ggagttatcg ctgtggatct tgctaaagac     780
atgttgttgg tacataggaa cacttatgcg gttgttgttt ctactgagaa cattactcag     840
aattggtatt tggtaacaa gaaatcgatg ttgataccga actgcttgtt tcgagttggt     900
ggctctgcgg ttttgctatc gaacaagtcg agggacaaga gacggtctaa gtacaggctt     960
gtacatgtag tcaggactca ccgtggagca gatgataaag ctttccgttg tgttatcaa    1020 gagcaggatg atacagggag aaccgggggtt cgttgtcga aagatctaat ggcgattgca    1080
ggggaaactc tcaaaaccaa tatcactaca ttgggtcctc ttgttctacc gataagtgag    1140
```

```
cagattctct tctttatgac tctagttgtg aagaagctct ttaacggtaa agtgaaaccg   1200
tatatcccgg atttcaaact tgctttcgag catttctgta tccatgctgg tggaagagct   1260
gtgatcgatg agttagagaa gaatctgcag ctttcaccag ttcatgtcga ggcttcgagg   1320
atgactcttc atcgatttgg taacacatct tcgagctcca tttggtatga attggcttac   1380
attgaagcga agggaaggat gcgaagaggt aatcgtgttt ggcaaatcgc gttcggaagt   1440
ggatttaaat gtaatagcgc gatttgggaa gcattaaggc atgtgaaacc ttcgaacaac   1500
agtccttggg aagattgtat tgacaagtat ccggtaactt taagttat              1548
```

<210> SEQ ID NO 14
<211> LENGTH: 516
<212> TYPE: PRT
<213> ORGANISM: Arabidopsis thaliana

<400> SEQUENCE: 14

```
Met Asp Gly Ala Gly Glu Ser Arg Leu Gly Asp Gly Gly Gly Asp
 1               5                  10                  15

Gly Ser Val Gly Val Gln Ile Arg Gln Thr Arg Met Leu Pro Asp Phe
            20                  25                  30

Leu Gln Ser Val Asn Leu Lys Tyr Val Lys Leu Gly Tyr His Tyr Leu
         35                  40                  45

Ile Ser Asn Leu Leu Thr Leu Cys Leu Phe Pro Leu Ala Val Val Ile
     50                  55                  60

Ser Val Glu Ala Ser Gln Met Asn Pro Asp Asp Leu Lys Gln Leu Trp
 65                  70                  75                  80

Ile His Leu Gln Tyr Asn Leu Val Ser Ile Ile Cys Ser Ala Ile
                 85                  90                  95

Leu Val Phe Gly Leu Thr Val Tyr Val Met Thr Arg Pro Arg Pro Val
            100                 105                 110

Tyr Leu Val Asp Phe Ser Cys Tyr Leu Pro Pro Asp His Leu Lys Ala
        115                 120                 125

Pro Tyr Ala Arg Phe Met Glu His Ser Arg Leu Thr Gly Asp Phe Asp
    130                 135                 140

Asp Ser Ala Leu Glu Phe Gln Arg Lys Ile Leu Glu Arg Ser Gly Leu
145                 150                 155                 160

Gly Glu Asp Thr Tyr Val Pro Glu Ala Met His Tyr Val Pro Pro Arg
                165                 170                 175

Ile Ser Met Ala Ala Ala Arg Glu Glu Ala Glu Gln Val Met Phe Gly
            180                 185                 190

Ala Leu Asp Asn Leu Phe Ala Asn Thr Asn Val Lys Pro Lys Asp Ile
        195                 200                 205

Gly Ile Leu Val Val Asn Cys Ser Leu Phe Asn Pro Thr Pro Ser Leu
    210                 215                 220

Ser Ala Met Ile Val Asn Lys Tyr Lys Leu Arg Gly Asn Ile Arg Ser
225                 230                 235                 240

Tyr Asn Leu Gly Gly Met Gly Cys Ser Ala Gly Val Ile Ala Val Asp
                245                 250                 255

Leu Ala Lys Asp Met Leu Leu Val His Arg Asn Thr Tyr Ala Val Val
            260                 265                 270

Val Ser Thr Glu Asn Ile Thr Gln Asn Trp Tyr Phe Gly Asn Lys Lys
        275                 280                 285

Ser Met Leu Ile Pro Asn Cys Leu Phe Arg Val Gly Gly Ser Ala Val
    290                 295                 300
```

```
Leu Leu Ser Asn Lys Ser Arg Asp Lys Arg Ser Lys Tyr Arg Leu
305                 310                 315                 320

Val His Val Val Arg Thr His Arg Gly Ala Asp Asp Lys Ala Phe Arg
            325                 330                 335

Cys Val Tyr Gln Glu Gln Asp Asp Thr Gly Arg Thr Gly Val Ser Leu
            340                 345                 350

Ser Lys Asp Leu Met Ala Ile Ala Gly Glu Thr Leu Lys Thr Asn Ile
            355                 360                 365

Thr Thr Leu Gly Pro Leu Val Leu Pro Ile Ser Glu Gln Ile Leu Phe
        370                 375                 380

Phe Met Thr Leu Val Val Lys Lys Leu Phe Asn Gly Lys Val Lys Pro
385                 390                 395                 400

Tyr Ile Pro Asp Phe Lys Leu Ala Phe Glu His Phe Cys Ile His Ala
            405                 410                 415

Gly Gly Arg Ala Val Ile Asp Glu Leu Glu Lys Asn Leu Gln Leu Ser
            420                 425                 430

Pro Val His Val Glu Ala Ser Arg Met Thr Leu His Arg Phe Gly Asn
        435                 440                 445

Thr Ser Ser Ser Ser Ile Trp Tyr Glu Leu Ala Tyr Ile Glu Ala Lys
    450                 455                 460

Gly Arg Met Arg Arg Gly Asn Arg Val Trp Gln Ile Ala Phe Gly Ser
465                 470                 475                 480

Gly Phe Lys Cys Asn Ser Ala Ile Trp Glu Ala Leu Arg His Val Lys
            485                 490                 495

Pro Ser Asn Asn Ser Pro Trp Glu Asp Cys Ile Asp Lys Tyr Pro Val
            500                 505                 510

Thr Leu Ser Tyr
        515

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
ctcgaggagc aatgacgtcc gttaa                                    25

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
ctcgagttag gaccgaccgt tttg                                     24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ctcgagcaag tccactacca cgca                                     24
```

```
<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
ctcgagcgag tcagaaggaa caaa                                          24

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
gataatttag agaggcacag ggt                                           23

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
gtcgacacaa gaatgggtag atccaa                                        26

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
cagttcctca aacgaagcta                                               20

<210> SEQ ID NO 22
<211> LENGTH: 27
<212> TYPE: DNA
<213> ORGANISM: Artificial Sequence
<220> FEATURE:
<223> OTHER INFORMATION: Primer

<400> SEQUENCE: 22
gtcgacttct caatggacgg tgccgga                                   27
```

What is claimed is:

1. An isolated polynucleotide encoding a polypeptide having an amino acid sequence selected from the group consisting of: SEQ ID NO:2, SEQ ID NO:4, SEQ ID NO:6, SEQ ID NO:12, and SEQ ID NO:14.

2. The polynucleotide of claim 1, wherein said amino acid sequence is SEQ ID NO:2.

3. The polynucleotide of claim 1, wherein said amino acid sequence is SEQ ID NO:4.

4. The polynucleotide of claim 1, wherein said amino acid sequence is SEQ ID NO:6.

5. The polynucleotide of claim 1, wherein said amino acid sequence is SEQ ID NO:12.

6. The polynucleotide of claim 1, wherein said amino acid sequence is SEQ ID NO:14.

7. An isolated polynucleotide, wherein said polynucleotide is selected from the group consisting of:
a) SEQ ID NO:1;
b) SEQ ID NO:3;
c) SEQ ID NO:5;
d) SEQ ID NO:7;
e) SEQ ID NO:9;
f) SEQ ID NO:11;
g) SEQ ID NO:13;
h) an RNA analog of SEQ ID NO:1;
i) an RNA analog of SEQ ID NO:3;
j) an RNA analog of SEQ ID NO:5;
k) an RNA analog of SEQ ID NO:7;

l) an RNA analog of SEQ ID NO:9;

m) an RNA analog of SEQ ID NO:11;

n) an RNA analog of SEQ ID NO:13;

o) a polynucleotide having a nucleic acid sequence complementary to a), b), c), d), e), f), g), h), i), j), k), l), m), or n); and p) a nucleic acid fragment of a), b), c), f), g), h), i), j), m), n), or o) that is at least 100 nucleotides in length.

8. A transgenic plant containing a nucleic acid construct comprising a polynucleotide selected from the group consisting of:

a) SEQ ID NO:1;

b) SEQ ID NO:3;

c) SEQ ID NO:5;

d) SEQ ID NO:7;

e) SEQ ID NO:9;

f) SEQ ID NO:11;

g) SEQ ID NO:13;

h) an RNA analog of SEQ ID NO:1;

i) an RNA analog of SEQ ID NO:3;

j) an RNA analog of SEQ ID NO:5;

k) an RNA analog of SEQ ID NO:7;

l) an RNA analog of SEQ ID NO:9;

m) an RNA analog of SEQ ID NO:11;

n) an RNA analog of SEQ ID NO:13;

o) a polynucleotide having a nucleic acid sequence complementary to a), b), c), d), e), f), g), h), i), j), k), l), m), or n); and p) a nucleic acid fragment of a), b), c), f), g), h), i), j), m), n), or o) that is at least 100 nucleotides in length.

9. The plant of claim 8, wherein said construct further comprises a regulatory element operably linked to said polynucleotide.

10. The plant of claim 9, wherein said regulatory element is a tissue-specific promoter.

11. The plant of claim 10, wherein said regulatory element is an epidermal cell-specific promoter.

12. The plant of claim 10, wherein said regulatory element is a seed-specific promoter that is operably linked in sense orientation to said polynucleotide.

13. The plant of claim 12, wherein said plant has altered levels of very long chain fatty acids in seeds compared to the levels in a plant lacking said nucleic acid construct.

14. A transgenic plant containing a nucleic acid construct comprising a polynucleotide encoding a polypeptide having an amino acid sequence selected from the group consisting of: SEQ ID NO:2, SEQ ID NO:4, SEQ ID NO:6, SEQ ID NO:8, SEQ ID NO:10, SEQ ID NO:12, and SEQ ID NO:14.

15. The plant of claim 14, wherein said construct further comprises a regulatory element operably linked to said polynucleotide.

16. The plant of claim 15, wherein said regulatory element is a tissue-specific promoter.

17. The plant of claim 16, wherein said regulatory element is an epidermal cell-specific promoter.

18. The plant of claim 16, wherein said regulatory element is a seed-specific promoter that is operably linked in sense orientation to said polynucleotide.

19. The plant of claim 18, wherein said plant has altered levels of very long chain fatty acids in seeds compared to the levels in a plant lacking said nucleic acid construct.

20. A method of altering the levels of very long chain fatty acids in a plant, comprising the steps of:

a) creating a nucleic acid construct, said construct comprising a polynucleotide selected from the group consisting of:

a) SEQ ID NO:1;

b) SEQ ID NO:3;

c) SEQ ID NO:5;

d) SEQ ID NO:7;

e) SEQ ID NO:9;

f) SEQ ID NO:11;

g) SEQ ID NO:13;

h) an RNA analog of SEQ ID NO:1;

i) an RNA analog of SEQ ID NO:3;

j) an RNA analog of SEQ ID NO:5;

k) an RNA analog of SEQ ID NO:7;

l) an RNA analog of SEQ ID NO:9;

m) an RNA analog of SEQ ID NO:11;

n) an RNA analog of SEQ ID NO:13;

o) a polynucleotide having a nucleic acid sequence complementary to a), b), c), d), e), f), g), h), i), j), k), l), m), or n); and p) a nucleic acid fragment of a), b), c), f), g), h), i), j), m), n), or o) that is at least 100 nucleotides in length; and b) introducing said construct into said plant, wherein said polynucleotide is effective for altering the levels of very long chain fatty acids in said plant.

21. An isolated polynucleotide encoding a polypeptide having the amino acid sequence of SEQ ID NO:8.

22. An isolated polynucleotide encoding a polypeptide having the amino acid sequence of SEQ ID NO:10.

23. The plant of claim 10, wherein said nucleic acid construct comprises a nucleic acid fragment of SEQ ID NO:1 that is at least 100 nucleotides in length.

24. The plant of claim 23, wherein said regulatory element is an epidermal cell-specific promoter.

25. The plant of claim 23, wherein said nucleic acid fragment is operably linked in antisense orientation to said regulatory element.

26. The plant of claim 10, wherein said nucleic acid construct comprises a nucleic acid fragment of SEQ ID NO:3 that is at least 100 nucleotides in length.

27. The plant of claim 26, wherein said regulatory element is an epidermal cell-specific promoter.

28. The plant of claim 26, wherein said nucleic acid fragment is operably linked in antisense orientation to said regulatory element.

29. The plant of claim 10, wherein said nucleic acid construct comprises a nucleic acid fragment of SEQ ID NO:5 that is at least 100 nucleotides in length.

30. The plant of claim 29, wherein said regulatory element is an epidermal cell-specific promoter.

31. The plant of claim 29, wherein said nucleic acid fragment is operably linked in antisense orientation to said regulatory element.

32. The plant of claim 10, wherein said nucleic acid construct comprises a nucleic acid fragment of SEQ ID NO:7 that is at least 100 nucleotides in length.

33. The plant of claim 32, wherein said regulatory element is an epidermal cell-specific promoter.

34. The plant of claim 32, wherein said nucleic acid fragment is operably linked in antisense orientation to said regulatory element.

35. The plant of claim 10, wherein said nucleic acid construct comprises a nucleic acid fragment of SEQ ID NO:9 that is at least 100 nucleotides in length.

36. The plant of claim 35, wherein said regulatory element is an epidermal cell-specific promoter.

37. The plant of claim 35, wherein said nucleic acid fragment is operably linked in antisense orientation to said regulatory element.

38. The plant of claim 10, wherein said nucleic acid construct comprises a nucleic acid fragment of SEQ ID NO:11 that is at least 100 nucleotides in length.

39. The plant of claim 38, wherein said regulatory element is an epidermal cell-specific promoter.

40. The plant of claim 38, wherein said nucleic acid fragment is operably linked in antisense orientation to said regulatory element.

41. The plant of claim 10, wherein said nucleic acid construct comprises a nucleic acid fragment of SEQ ID NO:13 that is at least 100 nucleotides in length.

42. The plant of claim 41, wherein said regulatory element is an epidermal cell-specific promoter.

43. The plant of claim 41, wherein said nucleic acid fragment is operably linked in antisense orientation to said regulatory element.

44. The plant of claim 16, wherein said regulatory element is operably linked in sense orientation to a polynucleotide encoding a polypeptide having the amino acid sequence of SEQ ID NO:2.

45. The plant of claim 16, wherein said regulatory element is operably linked in sense orientation to a polynucleotide encoding a polypeptide having the amino acid sequence of SEQ ID NO:4.

46. The plant of claim 16, wherein said regulatory element is operably linked in sense orientation to a polynucleotide encoding a polypeptide having the amino acid sequence of SEQ ID NO:6.

47. The plant of claim 16, wherein said regulatory element is operably linked in sense orientation to a polynucleotide encoding a polypeptide having the amino acid sequence of SEQ ID NO:8.

48. The plant of claim 16, wherein said regulatory element is operably linked in sense orientation to a polynucleotide encoding a polypeptide having the amino acid sequence of SEQ ID NO:10.

49. The plant of claim 16, wherein said regulatory element is operably linked in sense orientation to a polynucleotide encoding a polypeptide having the amino acid sequence of SEQ ID NO:12.

50. The plant of claim 16, wherein said regulatory element is operably linked in sense orientation to a polynucleotide encoding a polypeptide having the amino acid sequence of SEQ ID NO:14.

51. The plant of claim 17, wherein said regulatory element is operably linked in sense orientation to a polynucleotide encoding a polypeptide having the amino acid sequence of SEQ ID NO:2.

52. The plant of claim 17, wherein said regulatory element is operably linked in sense orientation to a polynucleotide encoding a polypeptide having the amino acid sequence of SEQ ID NO:4.

53. The plant of claim 17, wherein said regulatory element is operably linked in sense orientation to a polynucleotide encoding a polypeptide having the amino acid sequence of SEQ ID NO:6.

54. The plant of claim 17, wherein said regulatory element is operably linked in sense orientation to a polynucleotide encoding a polypeptide having the amino acid sequence of SEQ ID NO:8.

55. The plant of claim 17, wherein said regulatory element is operably linked in sense orientation to a polynucleotide encoding a polypeptide having the amino acid sequence of SEQ ID NO:10.

56. The plant of claim 17, wherein said regulatory element is operably linked in sense orientation to a polynucleotide encoding a polypeptide having the amino acid sequence of SEQ ID NO:12.

57. The plant of claim 17, wherein said regulatory element is operably linked in sense orientation to a polynucleotide encoding a polypeptide having the amino acid sequence of SEQ ID NO:14.

58. The plant of claim 18, wherein said polynucleotide encodes a polypeptide having the amino acid sequence of SEQ ID NO:2.

59. The plant of claim 18, wherein said polynucleotide encodes a polypeptide having the amino acid sequence of SEQ ID NO:4.

60. The plant of claim 18, wherein said polynucleotide encodes a polypeptide having the amino acid sequence of SEQ ID NO:6.

61. The plant of claim 18, wherein said polynucleotide encodes a polypeptide having the amino acid sequence of SEQ ID NO:8.

62. The plant of claim 18, wherein said polynucleotide encodes a polypeptide having the amino acid sequence of SEQ ID NO:10.

63. The plant of claim 18, wherein said polynucleotide encodes a polypeptide having the amino acid sequence of SEQ ID NO:12.

64. The plant of claim 18, wherein said polynucleotide encodes a polypeptide having the amino acid sequence of SEQ ID NO:14.

\* \* \* \* \*